United States Patent
Hafezi et al.

(10) Patent No.: US 10,588,544 B2
(45) Date of Patent: Mar. 17, 2020

(54) HIGHLY RELIABLE INGESTIBLE EVENT MARKERS AND METHODS FOR USING THE SAME

(71) Applicant: Proteus Digital Health, Inc., Redwood City, CA (US)

(72) Inventors: Hooman Hafezi, Redwood City, CA (US); Kit Yee Au-Yeung, San Francisco, CA (US); Robert Duck, San Francisco, CA (US); Maria Holen, Santa Clara, CA (US); Timothy Robertson, Belmont, CA (US); Benedict Costello, Berkeley, CA (US)

(73) Assignee: Proteus Digital Health, Inc., Redwood City, CA (US)

(*) Notice: Subject to any disclaimer, the term of this patent is extended or adjusted under 35 U.S.C. 154(b) by 192 days.

(21) Appl. No.: 15/050,733

(22) Filed: Feb. 23, 2016

(65) Prior Publication Data
US 2017/0014046 A1 Jan. 19, 2017

Related U.S. Application Data

(63) Continuation of application No. 13/756,280, filed on Jan. 31, 2013, now Pat. No. 9,320,455, which is a (Continued)

(51) Int. Cl.
*A61B 5/00* (2006.01)
*A61B 5/07* (2006.01)
(Continued)

(52) U.S. Cl.
CPC ............ *A61B 5/073* (2013.01); *A61B 5/0031* (2013.01); *A61B 5/065* (2013.01);
(Continued)

(58) Field of Classification Search
None
See application file for complete search history.

(56) References Cited

U.S. PATENT DOCUMENTS

| | | | |
|---|---|---|---|
| 1,548,459 | A | 8/1925 | Hammer |
| 2,587,158 | A | 2/1952 | Hofberg |

(Continued)

FOREIGN PATENT DOCUMENTS

| | | |
|---|---|---|
| CN | 1588649 | 3/2005 |
| CN | 1650844 | 8/2005 |

(Continued)

OTHER PUBLICATIONS

AADE, "AADE 37th Annual Meeting San Antonio Aug. 4-7, 2010" American Association of Diabetes Educators (2010); http://www.diabeteseducator.org/annualmeeting/2010/index.html; 2 pp.

(Continued)

*Primary Examiner* — Lori A. Clow
*Assistant Examiner* — Marie Archer
(74) *Attorney, Agent, or Firm* — K&L Gates LLP

(57) ABSTRACT

Ingestible event markers having high reliability are provided. Aspects of the ingestible event markers include a support, a control circuit, a first electrochemical material, a second electrochemical material and a membrane. In addition, the ingestible event markers may include one or more components that impart high reliability to the ingestible event marker. Further, the ingestible event markers may include an active agent. In some aspects, the active agent, such as a pharmaceutically active agent or a diagnostic agent may be associated with the membrane.

16 Claims, 6 Drawing Sheets

Related U.S. Application Data continuation of application No. 12/744,642, filed as application No. PCT/US2010/032590 on Apr. 27, 2010, now Pat. No. 8,545,402.

(60) Provisional application No. 61/173,511, filed on Apr. 28, 2009, provisional application No. 61/173,564, filed on Apr. 28, 2009.

(51) Int. Cl.
| | |
|---|---|
| *A61B 5/145* | (2006.01) |
| *H01M 2/02* | (2006.01) |
| *H01M 2/14* | (2006.01) |
| *A61K 9/00* | (2006.01) |
| *A61B 5/06* | (2006.01) |
| *H01M 6/34* | (2006.01) |

(52) U.S. Cl.
CPC ........ *A61B 5/14546* (2013.01); *A61B 5/4848* (2013.01); *A61B 5/6861* (2013.01); *A61B 5/6882* (2013.01); *A61K 9/0053* (2013.01); *A61K 9/0097* (2013.01); *H01M 2/025* (2013.01); *H01M 2/14* (2013.01); *H01M 6/34* (2013.01); *A61B 5/14539* (2013.01); *A61B 2560/0209* (2013.01); *A61B 2560/0214* (2013.01); *A61B 2562/02* (2013.01); *A61B 2562/162* (2013.01)

(56) References Cited

U.S. PATENT DOCUMENTS

| | | |
|---|---|---|
| 2,973,555 A | 3/1961 | Schwepke |
| 3,048,526 A | 8/1962 | Boswell |
| 3,079,824 A | 3/1963 | Schott |
| 3,096,248 A | 7/1963 | Rudzki |
| 3,176,399 A | 4/1965 | Marino et al. |
| 3,589,943 A | 6/1971 | Grubb et al. |
| 3,607,788 A | 9/1971 | Adolph |
| 3,642,008 A | 2/1972 | Bolduc |
| 3,679,480 A | 7/1972 | Brown et al. |
| 3,682,160 A | 8/1972 | Murata |
| 3,719,183 A | 3/1973 | Schwartz |
| 3,799,802 A | 3/1974 | Schneble, Jr. et al. |
| 3,828,766 A | 8/1974 | Krasnow |
| 3,837,339 A | 9/1974 | Aisenberg et al. |
| 3,849,041 A | 11/1974 | Knapp |
| 3,893,111 A | 7/1975 | Cotter |
| 3,944,064 A | 3/1976 | Bashaw et al. |
| 3,967,202 A | 6/1976 | Batz |
| 3,989,050 A | 11/1976 | Buchalter |
| 4,017,856 A | 4/1977 | Wiegand |
| 4,055,178 A | 10/1977 | Harrigan |
| 4,062,750 A | 12/1977 | Butler |
| 4,077,397 A | 3/1978 | Ellis |
| 4,077,398 A | 3/1978 | Ellis |
| 4,082,087 A | 4/1978 | Howson |
| 4,090,752 A | 5/1978 | Long |
| 4,106,348 A | 8/1978 | Auphan |
| 4,129,125 A | 12/1978 | Lester |
| 4,139,589 A | 2/1979 | Beringer et al. |
| 4,143,770 A | 3/1979 | Grimmell et al. |
| 4,166,453 A | 9/1979 | McClelland |
| 4,239,046 A | 12/1980 | Ong |
| 4,251,795 A | 2/1981 | Shibasaki et al. |
| 4,269,189 A | 5/1981 | Abraham |
| 4,331,654 A | 5/1982 | Morris |
| 4,345,588 A | 8/1982 | Widder et al. |
| 4,418,697 A | 12/1983 | Tama |
| 4,425,117 A | 1/1984 | Hugemann |
| 4,439,196 A | 3/1984 | Higuchi |
| 4,494,950 A | 1/1985 | Fischell |
| 4,559,950 A | 12/1985 | Vaughan |
| 4,564,363 A | 1/1986 | Bagnall et al. |
| 4,635,641 A | 1/1987 | Hoffman |
| 4,654,165 A | 3/1987 | Eisenber |
| 4,663,250 A | 5/1987 | Ong et al. |
| 4,669,479 A | 6/1987 | Dunseath |
| 4,687,660 A | 8/1987 | Baker et al. |
| 4,725,997 A | 2/1988 | Urquhart et al. |
| 4,749,575 A | 6/1988 | Rotman et al. |
| 4,763,659 A | 8/1988 | Dunseath |
| 4,767,627 A | 8/1988 | Caldwell et al. |
| 4,775,536 A | 10/1988 | Patell |
| 4,784,162 A | 11/1988 | Ricks |
| 4,793,825 A | 12/1988 | Benjamin et al. |
| 4,814,181 A | 3/1989 | Jordan et al. |
| 4,844,076 A | 7/1989 | Lesho |
| 4,847,090 A | 7/1989 | Della Posta et al. |
| 4,876,093 A | 10/1989 | Theeuwes et al. |
| 4,891,223 A * | 1/1990 | Ambegaonkar ....... A01N 25/26 424/408 |
| 4,896,261 A | 1/1990 | Nolan |
| 4,900,552 A | 2/1990 | Sanvordeker et al. |
| 4,975,230 A | 12/1990 | Pinkhasov |
| 4,987,897 A | 1/1991 | Funke |
| 5,000,957 A | 3/1991 | Eckenhoff et al. |
| 5,016,634 A | 5/1991 | Vock et al. |
| 5,018,335 A | 5/1991 | Yamamoto et al. |
| 5,079,006 A | 1/1992 | Urguhart |
| 5,110,441 A | 5/1992 | Kinlen et al. |
| 5,160,885 A | 11/1992 | Hannam et al. |
| 5,167,626 A | 12/1992 | Casper |
| 5,176,626 A | 1/1993 | Soehendra |
| 5,187,723 A | 2/1993 | Mueller |
| 5,213,738 A | 5/1993 | Hampton et al. |
| 5,218,343 A | 6/1993 | Stobbe et al. |
| 5,261,402 A | 11/1993 | DiSabito |
| 5,263,481 A | 11/1993 | Axelgaard et al. |
| 5,273,066 A | 12/1993 | Graham et al. |
| 5,279,607 A | 1/1994 | Schentag et al. |
| 5,281,287 A | 1/1994 | Lloyd |
| 5,283,136 A | 2/1994 | Peled et al. |
| 5,288,564 A | 2/1994 | Klein |
| 5,305,745 A | 4/1994 | Zacouto |
| 5,310,301 A | 5/1994 | Aono |
| 5,318,557 A | 6/1994 | Gross |
| 5,331,953 A | 7/1994 | Andersson et al. |
| 5,394,882 A | 3/1995 | Mawhinney |
| 5,395,366 A | 3/1995 | D'Andrea et al. |
| 5,436,091 A | 7/1995 | Shackle et al. |
| 5,443,461 A | 8/1995 | Atkinson et al. |
| 5,443,843 A | 8/1995 | Curatolo et al. |
| 5,458,141 A | 10/1995 | Neil et al. |
| 5,458,994 A | 10/1995 | Nesselbeck et al. |
| 5,485,841 A | 1/1996 | Watkin et al. |
| 5,506,248 A | 4/1996 | Nikfar et al. |
| 5,551,020 A | 8/1996 | Flax et al. |
| 5,567,210 A | 10/1996 | Bates et al. |
| 5,596,302 A | 1/1997 | Mastrocola et al. |
| 5,600,548 A | 2/1997 | Nguyen et al. |
| 5,603,363 A | 2/1997 | Nelson |
| 5,634,468 A | 6/1997 | Platt |
| 5,645,063 A | 7/1997 | Straka et al. |
| 5,659,247 A | 8/1997 | Clements |
| 5,703,463 A | 12/1997 | Smith |
| 5,705,189 A | 1/1998 | Lehmann et al. |
| 5,724,432 A | 3/1998 | Bouvet et al. |
| 5,738,708 A | 4/1998 | Peachey et al. |
| 5,740,811 A | 4/1998 | Hedberg |
| 5,757,326 A | 5/1998 | Koyama et al. |
| 5,772,575 A | 6/1998 | Lesinski et al. |
| 5,792,048 A | 8/1998 | Schaefer |
| 5,802,467 A | 9/1998 | Salazar |
| 5,833,716 A | 11/1998 | Bar-Or |
| 5,842,324 A | 12/1998 | Grosskopf et al. |
| 5,845,265 A | 12/1998 | Woolston |
| 5,862,803 A | 1/1999 | Besson |
| 5,868,136 A | 2/1999 | Fox |
| 5,914,132 A | 6/1999 | Kelm et al. |
| 5,914,701 A | 6/1999 | Gersheneld et al. |
| 5,925,030 A | 7/1999 | Gross et al. |
| 5,957,854 A | 9/1999 | Besson et al. |

(56) References Cited

U.S. PATENT DOCUMENTS

| | | |
|---|---|---|
| 5,963,132 A | 10/1999 | Yoakum et al. |
| 5,974,124 A | 10/1999 | Schlueter, Jr. et al. |
| 5,981,166 A | 11/1999 | Mandecki |
| 5,999,846 A | 12/1999 | Pardey et al. |
| 6,018,229 A | 1/2000 | Mitchell et al. |
| 6,038,464 A | 3/2000 | Axelgaard et al. |
| 6,042,710 A | 3/2000 | Dubrow |
| 6,047,203 A | 4/2000 | Sackner |
| 6,068,465 A | 5/2000 | Wilson |
| 6,068,589 A | 5/2000 | Neukermans |
| 6,076,016 A | 6/2000 | Feierbach et al. |
| 6,081,734 A | 6/2000 | Batz |
| 6,091,975 A | 7/2000 | Daddona et al. |
| 6,095,985 A | 8/2000 | Raymond et al. |
| 6,115,636 A | 9/2000 | Ryan |
| 6,122,351 A | 9/2000 | Schlueter, Jr. et al. |
| 6,141,592 A | 10/2000 | Pauly |
| 6,149,940 A | 11/2000 | Maggi et al. |
| 6,200,265 B1 | 3/2001 | Walsh et al. |
| 6,206,702 B1 | 3/2001 | Hayden et al. |
| 6,217,744 B1 | 4/2001 | Crosby |
| 6,231,593 B1 | 5/2001 | Meserol |
| 6,245,057 B1 | 6/2001 | Sieben et al. |
| 6,269,058 B1 | 7/2001 | Yamanoi et al. |
| 6,285,897 B1 | 9/2001 | Kilcoyne et al. |
| 6,287,252 B1 | 9/2001 | Lugo |
| 6,288,629 B1 | 9/2001 | Cofino et al. |
| 6,289,238 B1 | 9/2001 | Besson et al. |
| 6,315,719 B1 | 11/2001 | Rode et al. |
| 6,317,714 B1 | 11/2001 | Del Castillo |
| 6,342,774 B1 | 1/2002 | Kreisinger et al. |
| 6,344,824 B1 | 2/2002 | Takasugi et al. |
| 6,358,202 B1 | 3/2002 | Arent |
| 6,364,834 B1 | 4/2002 | Reuss |
| 6,366,206 B1 | 4/2002 | Ishikawa et al. |
| 6,371,927 B1 | 4/2002 | Brune |
| 6,374,670 B1 | 4/2002 | Spelman |
| 6,380,858 B1 | 4/2002 | Yarin et al. |
| 6,390,088 B1 | 5/2002 | Noehl et al. |
| 6,394,997 B1 | 5/2002 | Lemelson |
| 6,426,863 B1 | 7/2002 | Munshi |
| 6,432,292 B1 | 8/2002 | Pinto et al. |
| 6,440,069 B1 | 8/2002 | Raymond et al. |
| 6,441,747 B1 | 8/2002 | Khair |
| 6,453,199 B1 | 9/2002 | Kobozev |
| 6,477,424 B1 | 11/2002 | Thompson et al. |
| 6,496,705 B1 | 12/2002 | Ng et al. |
| 6,526,315 B1 | 2/2003 | Inagawa |
| 6,531,026 B1 | 3/2003 | Takeichi et al. |
| 6,544,174 B2 | 4/2003 | West |
| 6,547,994 B1 | 4/2003 | Monkhouse et al. |
| 6,564,079 B1 | 5/2003 | Cory |
| 6,567,685 B2 | 5/2003 | Takamori et al. |
| 6,572,636 B1 | 6/2003 | Hagen et al. |
| 6,577,893 B1 | 6/2003 | Besson et al. |
| 6,579,231 B1 | 6/2003 | Phipps |
| 6,595,929 B2 | 7/2003 | Stivoric |
| 6,599,284 B2 | 7/2003 | Faour et al. |
| 6,602,518 B2 | 8/2003 | Seielstad et al. |
| 6,605,038 B1 | 8/2003 | Teller |
| 6,609,018 B2 | 8/2003 | Cory |
| 6,612,984 B1 | 9/2003 | Kerr |
| 6,632,175 B1 | 10/2003 | Marshall |
| 6,632,216 B2 * | 10/2003 | Houzego .......... A61M 25/01 604/890.1 |
| 6,635,279 B2 | 10/2003 | Kolter et al. |
| 6,643,541 B2 | 11/2003 | Mok et al. |
| 6,654,638 B1 | 11/2003 | Sweeney |
| 6,663,846 B1 | 12/2003 | McCombs |
| 6,673,474 B2 | 1/2004 | Yamamoto |
| 6,680,923 B1 | 1/2004 | Leon |
| 6,689,117 B2 | 2/2004 | Sweeney et al. |
| 6,694,161 B2 | 2/2004 | Mehrotra |
| 6,704,602 B2 | 3/2004 | Berg et al. |
| 6,720,923 B1 | 4/2004 | Hayward et al. |
| 6,738,671 B2 | 5/2004 | Christophersom et al. |
| 6,740,033 B1 | 5/2004 | Olejniczak et al. |
| 6,745,082 B2 | 6/2004 | Axelgaard et al. |
| 6,755,783 B2 | 6/2004 | Cosentino |
| 6,757,523 B2 | 6/2004 | Fry |
| 6,759,968 B2 | 7/2004 | Zierolf |
| 6,767,200 B2 | 7/2004 | Sowden et al. |
| 6,773,429 B2 | 8/2004 | Sheppard et al. |
| 6,800,060 B2 | 10/2004 | Marshall |
| 6,801,137 B2 | 10/2004 | Eggers et al. |
| 6,816,794 B2 | 11/2004 | Alvi |
| 6,822,554 B2 | 11/2004 | Vrijens et al. |
| 6,824,512 B2 | 11/2004 | Warkentin et al. |
| 6,836,862 B1 | 12/2004 | Erekson et al. |
| 6,839,659 B2 | 1/2005 | Tarassenko et al. |
| 6,840,904 B2 | 1/2005 | Goldberg |
| 6,842,636 B2 | 1/2005 | Perrault |
| 6,845,272 B1 | 1/2005 | Thomsen |
| 6,864,780 B2 | 3/2005 | Doi |
| 6,879,810 B2 | 4/2005 | Bouet |
| 6,888,337 B2 | 5/2005 | Sawyers |
| 6,889,165 B2 | 5/2005 | Lind et al. |
| 6,909,878 B2 | 6/2005 | Haller |
| 6,922,592 B2 | 7/2005 | Thompson et al. |
| 6,928,370 B2 | 8/2005 | Anuzis et al. |
| 6,929,636 B1 | 8/2005 | Von Alten |
| 6,937,150 B2 | 8/2005 | Medema |
| 6,942,616 B2 | 9/2005 | Kerr |
| 6,942,770 B2 | 9/2005 | Cai et al. |
| 6,946,156 B2 | 9/2005 | Bunick |
| 6,951,536 B2 | 10/2005 | Yokoi |
| 6,957,107 B2 | 10/2005 | Rogers et al. |
| 6,958,603 B2 | 10/2005 | Kondo |
| 6,960,617 B2 | 11/2005 | Omidian et al. |
| 6,968,153 B1 | 11/2005 | Heinonen |
| 6,977,511 B2 | 12/2005 | Patel et al. |
| 6,982,094 B2 | 1/2006 | Sowden |
| 6,987,965 B2 | 1/2006 | Ng et al. |
| 6,990,082 B1 | 1/2006 | Zehavi et al. |
| 7,002,476 B2 | 2/2006 | Rapchak |
| 7,004,395 B2 | 2/2006 | Koenck |
| 7,009,634 B2 | 3/2006 | Iddan et al. |
| 7,009,946 B1 | 3/2006 | Kardach |
| 7,013,162 B2 | 3/2006 | Gorsuch |
| 7,016,648 B2 | 3/2006 | Haller |
| 7,020,508 B2 | 3/2006 | Stivoric |
| 7,024,248 B2 | 4/2006 | Penner et al. |
| 7,031,745 B2 | 4/2006 | Shen |
| 7,031,857 B2 | 4/2006 | Tarassenko et al. |
| 7,039,453 B2 | 5/2006 | Mullick |
| 7,044,911 B2 | 5/2006 | Drinan et al. |
| 7,046,649 B2 | 5/2006 | Awater et al. |
| 7,061,236 B2 | 6/2006 | Britton |
| 7,083,578 B2 | 8/2006 | Lewkowicz |
| 7,116,252 B2 | 10/2006 | Teraguchi |
| 7,118,531 B2 | 10/2006 | Krill |
| 7,122,143 B2 | 10/2006 | Sowden et al. |
| 7,127,300 B2 | 10/2006 | Mazar et al. |
| 7,146,228 B2 | 12/2006 | Nielsen |
| 7,146,449 B2 | 12/2006 | Do et al. |
| 7,149,581 B2 | 12/2006 | Goedeke et al. |
| 7,154,071 B2 | 12/2006 | Sattler et al. |
| 7,155,232 B2 | 12/2006 | Godfrey et al. |
| 7,160,258 B2 | 1/2007 | Imran |
| 7,164,942 B2 | 1/2007 | Avrahami |
| 7,171,166 B2 | 1/2007 | Ng et al. |
| 7,171,177 B2 | 1/2007 | Park et al. |
| 7,171,259 B2 | 1/2007 | Rytky |
| 7,176,784 B2 | 2/2007 | Gilbert et al. |
| 7,187,960 B2 | 3/2007 | Abreu |
| 7,188,199 B2 | 3/2007 | Leung et al. |
| 7,188,767 B2 | 3/2007 | Penuela |
| 7,192,397 B2 * | 3/2007 | Lewkowicz ........ A61B 1/00082 600/160 |
| 7,194,038 B1 | 3/2007 | Inkinen |
| 7,196,495 B1 | 3/2007 | Burcham |
| 7,206,630 B1 | 4/2007 | Tarler |
| 7,209,790 B2 | 4/2007 | Thompson et al. |
| 7,215,660 B2 | 5/2007 | Perlman |

(56) References Cited

U.S. PATENT DOCUMENTS

| | | |
|---|---|---|
| 7,215,991 B2 | 5/2007 | Besson |
| 7,218,967 B2 | 5/2007 | Bergelson |
| 7,231,451 B2 | 6/2007 | Law |
| 7,243,118 B2 | 7/2007 | Lou |
| 7,246,521 B2 | 7/2007 | Kim |
| 7,249,212 B2 | 7/2007 | Do |
| 7,252,792 B2 | 8/2007 | Perrault |
| 7,253,716 B2 | 8/2007 | Lovoi et al. |
| 7,261,690 B2 | 8/2007 | Teller |
| 7,270,633 B1 | 9/2007 | Goscha |
| 7,273,454 B2 | 9/2007 | Raymond et al. |
| 7,289,855 B2 | 10/2007 | Nghiem |
| 7,291,497 B2 | 11/2007 | Holmes |
| 7,292,139 B2 | 11/2007 | Mazar et al. |
| 7,294,105 B1 | 11/2007 | Islam |
| 7,311,665 B2 | 12/2007 | Hawthorne |
| 7,313,163 B2 | 12/2007 | Liu |
| 7,317,378 B2 | 1/2008 | Jarvis et al. |
| 7,318,808 B2 | 1/2008 | Tarassenko et al. |
| 7,336,929 B2 | 2/2008 | Yasuda |
| 7,342,895 B2 | 3/2008 | Serpa |
| 7,346,380 B2 | 3/2008 | Axelgaard et al. |
| 7,349,722 B2 | 3/2008 | Witkowski et al. |
| 7,352,998 B2 | 4/2008 | Palin |
| 7,353,258 B2 | 4/2008 | Washburn |
| 7,357,891 B2 | 4/2008 | Yang et al. |
| 7,359,674 B2 | 4/2008 | Markki |
| 7,366,558 B2 | 4/2008 | Virtanen et al. |
| 7,368,190 B2 | 5/2008 | Heller et al. |
| 7,368,191 B2 | 5/2008 | Andelman et al. |
| 7,373,196 B2 | 5/2008 | Ryu et al. |
| 7,375,739 B2 | 5/2008 | Robbins |
| 7,376,435 B2 | 5/2008 | McGowan |
| 7,382,247 B2 | 6/2008 | Welch et al. |
| 7,382,263 B2 | 6/2008 | Danowski et al. |
| 7,387,607 B2 | 6/2008 | Holt |
| 7,388,903 B2 | 6/2008 | Godfrey et al. |
| 7,389,088 B2 | 6/2008 | Kim |
| 7,392,015 B1 | 6/2008 | Farlow |
| 7,395,106 B2 | 7/2008 | Ryu et al. |
| 7,396,330 B2 | 7/2008 | Banet |
| 7,404,968 B2 | 7/2008 | Abrams et al. |
| 7,413,544 B2 | 8/2008 | Kerr |
| 7,414,534 B1 | 8/2008 | Kroll et al. |
| 7,414,543 B2 | 8/2008 | Rye et al. |
| 7,415,242 B1 | 8/2008 | Ngan |
| 7,424,268 B2 | 9/2008 | Diener |
| 7,424,319 B2 | 9/2008 | Muehlsteff |
| 7,427,266 B2 | 9/2008 | Ayer et al. |
| 7,442,164 B2 | 10/2008 | Berrang et al. |
| 7,443,290 B2 | 10/2008 | Takiguchi |
| 7,458,887 B2 | 12/2008 | Kurosawa |
| 7,469,838 B2 | 12/2008 | Brooks et al. |
| 7,471,665 B2 | 12/2008 | Perlman |
| 7,471,992 B2 | 12/2008 | Schmidt et al. |
| 7,492,128 B2 | 2/2009 | Shen |
| 7,499,674 B2 | 3/2009 | Salokannel |
| 7,510,121 B2 | 3/2009 | Koenck |
| 7,512,448 B2 | 3/2009 | Malick |
| 7,515,043 B2 | 4/2009 | Welch |
| 7,519,416 B2 | 4/2009 | Sula et al. |
| 7,523,756 B2 | 4/2009 | Minai |
| 7,525,426 B2 | 4/2009 | Edelstein |
| 7,527,807 B2 | 5/2009 | Choi et al. |
| 7,537,590 B2 | 5/2009 | Santini, Jr. et al. |
| 7,539,533 B2 | 5/2009 | Tran |
| 7,542,878 B2 | 6/2009 | Nanikashvili |
| 7,547,278 B2 | 6/2009 | Miyazaki et al. |
| 7,551,590 B2 | 6/2009 | Haller |
| 7,554,452 B2 | 6/2009 | Cole |
| 7,558,620 B2 | 7/2009 | Ishibashi |
| 7,575,005 B2 | 8/2009 | Mumford |
| 7,616,111 B2 | 11/2009 | Covannon |
| 7,617,001 B2 | 11/2009 | Penner et al. |
| 7,626,387 B2 | 12/2009 | Adachi |
| 7,639,473 B2 | 12/2009 | Hsu et al. |
| 7,640,802 B2 | 1/2010 | King et al. |
| 7,645,262 B2 | 1/2010 | Greenberg et al. |
| 7,647,112 B2 | 1/2010 | Tracey |
| 7,647,185 B2 | 1/2010 | Tarassenko et al. |
| 7,653,031 B2 | 1/2010 | Godfrey et al. |
| 7,672,714 B2 | 3/2010 | Kuo |
| 7,673,679 B2 | 3/2010 | Harrison et al. |
| 7,678,043 B2 | 3/2010 | Gilad |
| 7,686,839 B2 | 3/2010 | Parker |
| 7,697,994 B2 | 4/2010 | VanDanacker et al. |
| 7,720,036 B2 | 5/2010 | Sadri |
| 7,729,776 B2 | 6/2010 | Von Arx et al. |
| 7,733,224 B2 | 6/2010 | Tran |
| 7,736,318 B2 | 6/2010 | Costentino |
| 7,756,587 B2 | 7/2010 | Penner et al. |
| 7,760,104 B2 | 7/2010 | Asp |
| 7,782,991 B2 | 8/2010 | Sobchak et al. |
| 7,796,043 B2 | 9/2010 | Euliano et al. |
| 7,797,033 B2 | 9/2010 | D'Andrea et al. |
| 7,809,399 B2 | 10/2010 | Lu |
| 7,844,341 B2 | 11/2010 | Von Arx et al. |
| 7,881,799 B2 | 2/2011 | Greenberg et al. |
| 7,975,587 B2 | 7/2011 | Schneider |
| 7,978,064 B2 | 7/2011 | Zdeblick et al. |
| 7,983,189 B2 | 7/2011 | Bugenhagen |
| 8,036,731 B2 | 10/2011 | Kimchy et al. |
| 8,036,748 B2 | 10/2011 | Zdeblick et al. |
| 8,054,047 B2 | 11/2011 | Chen et al. |
| 8,054,140 B2 | 11/2011 | Fleming et al. |
| 8,055,334 B2 | 11/2011 | Savage et al. |
| 8,082,919 B2 | 12/2011 | Brunnberg et al. |
| 8,119,045 B2 | 2/2012 | Schmidt et al. |
| 8,131,376 B1 | 3/2012 | Faraji et al. |
| 8,177,611 B2 | 5/2012 | Kang |
| 8,185,191 B1 | 5/2012 | Shapiro et al. |
| 8,185,646 B2 | 5/2012 | Headley |
| 8,200,320 B2 | 6/2012 | Kovacs |
| 8,207,731 B2 | 6/2012 | Moskalenko |
| 8,224,596 B2 | 7/2012 | Agrawal et al. |
| 8,253,586 B1 | 8/2012 | Matak |
| 8,254,853 B2 | 8/2012 | Rofougaran |
| 8,271,146 B2 | 9/2012 | Heber et al. |
| 8,298,574 B2 | 10/2012 | Tsabari et al. |
| 8,343,068 B2 | 1/2013 | Najafi et al. |
| 8,374,698 B2 | 2/2013 | Ok et al. |
| 8,389,003 B2 | 3/2013 | Mintchev et al. |
| 8,404,275 B2 | 3/2013 | Habboushe |
| 8,425,492 B2 | 4/2013 | Herbert et al. |
| 8,443,214 B2 | 5/2013 | Lee et al. |
| 8,454,528 B2 | 6/2013 | Yuen et al. |
| 8,532,776 B2 | 9/2013 | Greenberg et al. |
| 8,540,664 B2 | 9/2013 | Robertson et al. |
| 8,547,248 B2 | 10/2013 | Zdeblick et al. |
| 8,558,563 B2 | 10/2013 | Zdeblick |
| 8,564,432 B2 | 10/2013 | Covannon et al. |
| 8,597,186 B2 | 12/2013 | Hafezi et al. |
| 8,634,838 B2 | 1/2014 | Hellwig et al. |
| 8,647,358 B2 | 2/2014 | Brister et al. |
| 8,660,645 B2 | 2/2014 | Stevenson et al. |
| 8,668,643 B2 | 3/2014 | Kinast |
| 8,685,451 B2 | 4/2014 | Toneguzzo et al. |
| 8,697,057 B2 | 4/2014 | Van Epps et al. |
| 8,698,006 B2 | 4/2014 | Bealka et al. |
| 8,758,237 B2 | 6/2014 | Sherman et al. |
| 8,784,308 B2 | 7/2014 | Duck et al. |
| 8,802,183 B2 | 8/2014 | Frank et al. |
| 8,816,847 B2 | 8/2014 | Zdeblick et al. |
| 8,836,513 B2 | 9/2014 | Hafezi et al. |
| 8,838,217 B2 | 9/2014 | Myr |
| 8,858,432 B2 | 10/2014 | Robertson |
| 8,908,943 B2 | 12/2014 | Berry et al. |
| 8,912,908 B2 | 12/2014 | Berkman et al. |
| 8,926,509 B2 | 1/2015 | Magar et al. |
| 8,932,221 B2 | 1/2015 | Colliou et al. |
| 8,945,005 B2 | 2/2015 | Hafezi et al. |
| 8,951,234 B2 | 2/2015 | Hafezi et al. |
| 8,989,837 B2 | 3/2015 | Weinstein et al. |
| 9,031,658 B2 | 5/2015 | Chiao et al. |

(56) References Cited

U.S. PATENT DOCUMENTS

| | | |
|---|---|---|
| 9,088,168 B2 | 7/2015 | Mach et al. |
| 9,107,806 B2 | 8/2015 | Hafezi et al. |
| 9,119,554 B2 | 9/2015 | Robertson et al. |
| 9,119,918 B2 | 9/2015 | Robertson et al. |
| 9,149,423 B2 | 10/2015 | Duck et al. |
| 9,158,890 B2 | 10/2015 | Meredith et al. |
| 9,161,707 B2 | 10/2015 | Hafezi et al. |
| 9,189,941 B2 | 11/2015 | Eschelman et al. |
| 9,226,663 B2 | 1/2016 | Fei |
| 9,226,679 B2 | 1/2016 | Balda |
| 9,268,909 B2 | 2/2016 | Jani et al. |
| 9,270,025 B2 | 2/2016 | Robertson et al. |
| 9,271,897 B2 | 3/2016 | Costello et al. |
| 9,277,864 B2 | 3/2016 | Yang et al. |
| 9,433,371 B2 | 9/2016 | Hafezi et al. |
| 9,439,599 B2 | 9/2016 | Thompson et al. |
| 9,517,012 B2 | 12/2016 | Lane et al. |
| 9,599,679 B2 | 3/2017 | Taylor et al. |
| 9,741,975 B2 | 8/2017 | Laulicht et al. |
| 9,756,874 B2 | 9/2017 | Arne et al. |
| 9,968,284 B2 | 5/2018 | Vidalis et al. |
| 2001/0027331 A1 | 10/2001 | Thompson |
| 2001/0044588 A1 | 11/2001 | Mault |
| 2001/0051766 A1 | 12/2001 | Gazdinski |
| 2002/0002326 A1 | 1/2002 | Causey et al. |
| 2002/0026111 A1 | 2/2002 | Ackerman |
| 2002/0032384 A1 | 3/2002 | Raymond et al. |
| 2002/0032385 A1 | 3/2002 | Raymond et al. |
| 2002/0040278 A1 | 4/2002 | Anuzis et al. |
| 2002/0077620 A1 | 6/2002 | Sweeney et al. |
| 2002/0128934 A1 | 9/2002 | Shaer |
| 2002/0132226 A1 | 9/2002 | Nair |
| 2002/0136744 A1 | 9/2002 | McGlynn et al. |
| 2002/0179921 A1 | 12/2002 | Cohn |
| 2002/0192159 A1 | 12/2002 | Reitberg |
| 2002/0193669 A1 | 12/2002 | Glukhovsky |
| 2002/0198470 A1 | 12/2002 | Imran et al. |
| 2003/0017826 A1 | 1/2003 | Fishman et al. |
| 2003/0023150 A1 | 1/2003 | Yokoi et al. |
| 2003/0028226 A1 | 2/2003 | Thompson |
| 2003/0062551 A1 | 4/2003 | Chen et al. |
| 2003/0065536 A1 | 4/2003 | Hansen |
| 2003/0076179 A1 | 4/2003 | Branch et al. |
| 2003/0083559 A1 | 5/2003 | Thompson |
| 2003/0091625 A1 | 5/2003 | Hariharan et al. |
| 2003/0126593 A1 | 7/2003 | Mault |
| 2003/0130714 A1 | 7/2003 | Nielsen et al. |
| 2003/0135128 A1 | 7/2003 | Suffin et al. |
| 2003/0135392 A1 | 7/2003 | Vrijens et al. |
| 2003/0152622 A1 | 8/2003 | Louie-Helm et al. |
| 2003/0158466 A1 | 8/2003 | Lynn et al. |
| 2003/0158756 A1 | 8/2003 | Abramson |
| 2003/0162556 A1 | 8/2003 | Libes |
| 2003/0164401 A1 | 9/2003 | Andreasson et al. |
| 2003/0167000 A1 | 9/2003 | Mullick et al. |
| 2003/0171791 A1 | 9/2003 | KenKnight |
| 2003/0171898 A1 | 9/2003 | Tarassenko et al. |
| 2003/0181788 A1 | 9/2003 | Yokoi et al. |
| 2003/0185286 A1 | 10/2003 | Yuen |
| 2003/0187337 A1 | 10/2003 | Tarassenko et al. |
| 2003/0187338 A1 | 10/2003 | Say et al. |
| 2003/0195403 A1 | 10/2003 | Berner et al. |
| 2003/0213495 A1 | 11/2003 | Fujita et al. |
| 2003/0214579 A1 | 11/2003 | Iddan |
| 2003/0216622 A1 | 11/2003 | Meron et al. |
| 2003/0216625 A1 | 11/2003 | Phipps |
| 2003/0216666 A1 | 11/2003 | Ericson et al. |
| 2003/0216729 A1 | 11/2003 | Marchitto |
| 2003/0219484 A1 | 11/2003 | Sowden et al. |
| 2003/0232895 A1 | 12/2003 | Omidian et al. |
| 2004/0008123 A1 | 1/2004 | Carrender et al. |
| 2004/0018476 A1 | 1/2004 | LaDue |
| 2004/0034295 A1 | 2/2004 | Salganicoff |
| 2004/0049245 A1 | 3/2004 | Gass |
| 2004/0073095 A1 | 4/2004 | Causey et al. |
| 2004/0073454 A1 | 4/2004 | Urquhart et al. |
| 2004/0077995 A1 | 4/2004 | Ferek-Petric |
| 2004/0082982 A1 | 4/2004 | Gord et al. |
| 2004/0087839 A1 | 5/2004 | Raymond et al. |
| 2004/0092801 A1 | 5/2004 | Drakulic |
| 2004/0106859 A1 | 6/2004 | Say et al. |
| 2004/0115507 A1 | 6/2004 | Potter et al. |
| 2004/0115517 A1 | 6/2004 | Fukada et al. |
| 2004/0121015 A1 | 6/2004 | Chidlaw et al. |
| 2004/0148140 A1 | 7/2004 | Tarassenko et al. |
| 2004/0153007 A1 | 8/2004 | Harris |
| 2004/0167226 A1 | 8/2004 | Serafini |
| 2004/0167465 A1 | 8/2004 | Mihai et al. |
| 2004/0167801 A1 | 8/2004 | Say et al. |
| 2004/0193020 A1 | 9/2004 | Chiba |
| 2004/0193029 A1 | 9/2004 | Gluhovsky |
| 2004/0193446 A1 | 9/2004 | Mayer et al. |
| 2004/0199222 A1 | 10/2004 | Sun et al. |
| 2004/0215084 A1 | 10/2004 | Shimizu et al. |
| 2004/0218683 A1 | 11/2004 | Batra |
| 2004/0220643 A1 | 11/2004 | Schmidt |
| 2004/0224644 A1 | 11/2004 | Wu |
| 2004/0225199 A1 | 11/2004 | Evanyk |
| 2004/0253304 A1 | 12/2004 | Gross et al. |
| 2004/0258571 A1 | 12/2004 | Lee et al. |
| 2004/0259899 A1 | 12/2004 | Sanghvi et al. |
| 2004/0260154 A1 | 12/2004 | Sidelnik |
| 2005/0003074 A1 | 1/2005 | Brown et al. |
| 2005/0017841 A1 | 1/2005 | Doi |
| 2005/0020887 A1 | 1/2005 | Goldberg |
| 2005/0021370 A1 | 1/2005 | Riff |
| 2005/0024198 A1 | 2/2005 | Ward |
| 2005/0027205 A1 | 2/2005 | Tarassenko et al. |
| 2005/0038321 A1 | 2/2005 | Fujita et al. |
| 2005/0043634 A1 | 2/2005 | Yokoi et al. |
| 2005/0043894 A1 | 2/2005 | Fernandez |
| 2005/0054897 A1 | 3/2005 | Hashimoto et al. |
| 2005/0055014 A1 | 3/2005 | Coppeta et al. |
| 2005/0062644 A1 | 3/2005 | Leci |
| 2005/0065407 A1 | 3/2005 | Nakamura et al. |
| 2005/0070778 A1 | 3/2005 | Lackey |
| 2005/0075145 A1 | 4/2005 | Dvorak et al. |
| 2005/0090753 A1 | 4/2005 | Goor et al. |
| 2005/0092108 A1 | 5/2005 | Andermo |
| 2005/0096514 A1 | 5/2005 | Starkebaum |
| 2005/0096562 A1 | 5/2005 | Delalic et al. |
| 2005/0101843 A1 | 5/2005 | Quinn |
| 2005/0101872 A1 | 5/2005 | Sattler |
| 2005/0115561 A1 | 6/2005 | Stahmann et al. |
| 2005/0116820 A1 | 6/2005 | Goldreich |
| 2005/0117389 A1 | 6/2005 | Worledge |
| 2005/0121322 A1 | 6/2005 | Say et al. |
| 2005/0131281 A1 | 6/2005 | Ayer et al. |
| 2005/0143623 A1 | 6/2005 | Kojima |
| 2005/0146594 A1 | 7/2005 | Nakatani et al. |
| 2005/0148883 A1 | 7/2005 | Boesen |
| 2005/0154428 A1 | 7/2005 | Bruinsma |
| 2005/0156709 A1 | 7/2005 | Gilbert et al. |
| 2005/0165323 A1 | 7/2005 | Montgomery |
| 2005/0177069 A1 | 8/2005 | Takizawa |
| 2005/0182389 A1 | 8/2005 | LaPorte |
| 2005/0187789 A1 | 8/2005 | Hatlestad et al. |
| 2005/0192489 A1 | 9/2005 | Marshall |
| 2005/0197680 A1 | 9/2005 | DelMain et al. |
| 2005/0208251 A1 | 9/2005 | Aisenbrey |
| 2005/0228268 A1 | 10/2005 | Cole |
| 2005/0234307 A1 | 10/2005 | Heinonen |
| 2005/0240305 A1 | 10/2005 | Bogash et al. |
| 2005/0245794 A1 | 11/2005 | Dinsmoor |
| 2005/0259768 A1 | 11/2005 | Yang et al. |
| 2005/0261559 A1 | 11/2005 | Mumford |
| 2005/0267556 A1 | 12/2005 | Shuros et al. |
| 2005/0267756 A1 | 12/2005 | Schultz et al. |
| 2005/0277912 A1 | 12/2005 | John |
| 2005/0277999 A1 | 12/2005 | Strother et al. |
| 2005/0279054 A1 | 12/2005 | Mauze et al. |
| 2005/0280539 A1 | 12/2005 | Pettus |
| 2005/0285746 A1 | 12/2005 | Sengupta |
| 2005/0288594 A1 | 12/2005 | Lewkowicz et al. |

(56) References Cited

U.S. PATENT DOCUMENTS

| | | |
|---|---|---|
| 2006/0001496 A1 | 1/2006 | Abrosimov et al. |
| 2006/0028727 A1 | 2/2006 | Moon et al. |
| 2006/0036134 A1 | 2/2006 | Tarassenko et al. |
| 2006/0058602 A1 | 3/2006 | Kwiatkowski et al. |
| 2006/0061472 A1 | 3/2006 | Lovoi et al. |
| 2006/0065713 A1 | 3/2006 | Kingery |
| 2006/0068006 A1 | 3/2006 | Begleiter |
| 2006/0074283 A1 | 4/2006 | Henderson |
| 2006/0074319 A1 | 4/2006 | Barnes et al. |
| 2006/0078765 A1 | 4/2006 | Yang et al. |
| 2006/0095091 A1 | 5/2006 | Drew |
| 2006/0095093 A1 | 5/2006 | Bettesh et al. |
| 2006/0100533 A1 | 5/2006 | Han |
| 2006/0109058 A1 | 5/2006 | Keating |
| 2006/0110962 A1 | 5/2006 | Powell |
| 2006/0122474 A1 | 6/2006 | Teller et al. |
| 2006/0122494 A1 | 6/2006 | Bouchoucha |
| 2006/0122667 A1 | 6/2006 | Chavan et al. |
| 2006/0129060 A1 | 6/2006 | Lee et al. |
| 2006/0136266 A1 | 6/2006 | Tarassenko et al. |
| 2006/0142648 A1 | 6/2006 | Banet |
| 2006/0145876 A1 | 7/2006 | Kimura |
| 2006/0148254 A1 | 7/2006 | McLean |
| 2006/0149339 A1 | 7/2006 | Burnes |
| 2006/0155174 A1 | 7/2006 | Glukhovsky et al. |
| 2006/0155183 A1 | 7/2006 | Kroecker |
| 2006/0161225 A1 | 7/2006 | Sormann et al. |
| 2006/0179949 A1 | 8/2006 | Kim |
| 2006/0183993 A1 | 8/2006 | Horn |
| 2006/0184092 A1 | 8/2006 | Atanasoska et al. |
| 2006/0204738 A1 | 9/2006 | Dubrow et al. |
| 2006/0210626 A1 | 9/2006 | Spaeder |
| 2006/0216603 A1 | 9/2006 | Choi |
| 2006/0218011 A1 | 9/2006 | Walker |
| 2006/0235489 A1 | 10/2006 | Drew |
| 2006/0243288 A1 | 11/2006 | Kim et al. |
| 2006/0247505 A1 | 11/2006 | Siddiqui |
| 2006/0253005 A1 | 11/2006 | Drinan |
| 2006/0270346 A1 | 11/2006 | Ibrahim |
| 2006/0273882 A1 | 12/2006 | Posamentier |
| 2006/0276702 A1 | 12/2006 | McGinnis |
| 2006/0280227 A1 | 12/2006 | Pinkney |
| 2006/0282001 A1 | 12/2006 | Noel |
| 2006/0289640 A1 | 12/2006 | Mercure |
| 2006/0293607 A1 | 12/2006 | Alt |
| 2007/0000776 A1 | 1/2007 | Karube et al. |
| 2007/0002038 A1 | 1/2007 | Suzuki |
| 2007/0006636 A1 | 1/2007 | King et al. |
| 2007/0008113 A1 | 1/2007 | Spoonhower et al. |
| 2007/0016089 A1 | 1/2007 | Fischell et al. |
| 2007/0027386 A1 | 2/2007 | Such |
| 2007/0027388 A1 | 2/2007 | Chou |
| 2007/0029195 A1 | 2/2007 | Li et al. |
| 2007/0038054 A1 | 2/2007 | Zhou |
| 2007/0049339 A1 | 3/2007 | Barak et al. |
| 2007/0055098 A1 | 3/2007 | Shimizu et al. |
| 2007/0060797 A1 | 3/2007 | Ball |
| 2007/0060800 A1 | 3/2007 | Drinan et al. |
| 2007/0066929 A1 | 3/2007 | Ferren et al. |
| 2007/0073353 A1 | 3/2007 | Rooney et al. |
| 2007/0096765 A1 | 5/2007 | Kagan |
| 2007/0106346 A1 | 5/2007 | Bergelson |
| 2007/0123772 A1 | 5/2007 | Euliano |
| 2007/0129622 A1 | 6/2007 | Bourget |
| 2007/0130287 A1 | 6/2007 | Kumar |
| 2007/0135803 A1 | 6/2007 | Belson |
| 2007/0142721 A1 | 6/2007 | Berner et al. |
| 2007/0156016 A1 | 7/2007 | Betesh |
| 2007/0160789 A1 | 7/2007 | Merical |
| 2007/0162089 A1 | 7/2007 | Mosesov |
| 2007/0162090 A1 | 7/2007 | Penner |
| 2007/0167495 A1 | 7/2007 | Brown et al. |
| 2007/0167848 A1 | 7/2007 | Kuo et al. |
| 2007/0173701 A1 | 7/2007 | Al-Ali |
| 2007/0179347 A1 | 8/2007 | Tarassenko et al. |
| 2007/0179371 A1 | 8/2007 | Peyser et al. |
| 2007/0185393 A1 | 8/2007 | Zhou |
| 2007/0191002 A1 | 8/2007 | Ge |
| 2007/0196456 A1 | 8/2007 | Stevens |
| 2007/0207793 A1 | 9/2007 | Myer |
| 2007/0208233 A1 | 9/2007 | Kovacs |
| 2007/0213659 A1 | 9/2007 | Trovato et al. |
| 2007/0237719 A1 | 10/2007 | Jones |
| 2007/0244370 A1 | 10/2007 | Kuo et al. |
| 2007/0255198 A1 | 11/2007 | Leong et al. |
| 2007/0255330 A1 | 11/2007 | Lee |
| 2007/0270672 A1 | 11/2007 | Hayter |
| 2007/0279217 A1 | 12/2007 | Venkatraman |
| 2007/0282174 A1 | 12/2007 | Sabatino |
| 2007/0282177 A1 | 12/2007 | Pilz |
| 2007/0299480 A1 | 12/2007 | Hill |
| 2008/0000804 A1 | 1/2008 | Carey et al. |
| 2008/0014866 A1 | 1/2008 | Lipowski |
| 2008/0020037 A1 | 1/2008 | Robertson et al. |
| 2008/0021519 A1 | 1/2008 | DeGeest |
| 2008/0021521 A1 | 1/2008 | Shah |
| 2008/0027679 A1 | 1/2008 | Shklarski |
| 2008/0033273 A1 | 2/2008 | Zhou |
| 2008/0038588 A1 | 2/2008 | Lee |
| 2008/0039700 A1 | 2/2008 | Drinan et al. |
| 2008/0045843 A1 | 2/2008 | Tsuji et al. |
| 2008/0046038 A1 | 2/2008 | Hill |
| 2008/0051647 A1 | 2/2008 | Wu et al. |
| 2008/0051667 A1 | 2/2008 | Goldreich |
| 2008/0058614 A1 | 3/2008 | Banet |
| 2008/0062856 A1 | 3/2008 | Feher |
| 2008/0065168 A1 | 3/2008 | Bitton et al. |
| 2008/0074307 A1 | 3/2008 | Boric-Lubecke |
| 2008/0077015 A1 | 3/2008 | Botic-Lubecke |
| 2008/0077028 A1 | 3/2008 | Schaldach et al. |
| 2008/0077188 A1 | 3/2008 | Denker et al. |
| 2008/0091089 A1 | 4/2008 | Guillory et al. |
| 2008/0091114 A1 | 4/2008 | Min |
| 2008/0097549 A1 | 4/2008 | Colbaugh |
| 2008/0097917 A1 | 4/2008 | Dicks |
| 2008/0103440 A1 | 5/2008 | Ferren et al. |
| 2008/0112885 A1 | 5/2008 | Okunev et al. |
| 2008/0114224 A1 | 5/2008 | Bandy et al. |
| 2008/0119705 A1 | 5/2008 | Patel |
| 2008/0119716 A1 | 5/2008 | Boric-Lubecke |
| 2008/0121825 A1 | 5/2008 | Trovato et al. |
| 2008/0137566 A1 | 6/2008 | Marholev |
| 2008/0139907 A1 | 6/2008 | Rao et al. |
| 2008/0140403 A1 | 6/2008 | Hughes et al. |
| 2008/0146871 A1 | 6/2008 | Arneson et al. |
| 2008/0146889 A1 | 6/2008 | Young |
| 2008/0146892 A1 | 6/2008 | LeBoeuf |
| 2008/0154104 A1 | 6/2008 | Lamego |
| 2008/0166992 A1 | 7/2008 | Ricordi |
| 2008/0175898 A1 | 7/2008 | Jones et al. |
| 2008/0183245 A1 | 7/2008 | Van Oort |
| 2008/0188837 A1 | 8/2008 | Belsky et al. |
| 2008/0194912 A1 | 8/2008 | Trovato et al. |
| 2008/0208009 A1 | 8/2008 | Shklarski |
| 2008/0214901 A1 | 9/2008 | Gehman |
| 2008/0214985 A1 | 9/2008 | Yanaki |
| 2008/0243020 A1 | 10/2008 | Chou |
| 2008/0249360 A1 | 10/2008 | Li |
| 2008/0262320 A1 | 10/2008 | Schaefer et al. |
| 2008/0262336 A1 | 10/2008 | Ryu |
| 2008/0269664 A1 | 10/2008 | Trovato et al. |
| 2008/0275312 A1 | 11/2008 | Mosesov |
| 2008/0284599 A1 | 11/2008 | Zdeblick et al. |
| 2008/0288027 A1 | 11/2008 | Kroll |
| 2008/0294020 A1 | 11/2008 | Sapounas |
| 2008/0299197 A1 | 12/2008 | Toneguzzo et al. |
| 2008/0300572 A1 | 12/2008 | Rankers |
| 2008/0303638 A1 | 12/2008 | Nguyen |
| 2008/0306357 A1 | 12/2008 | Korman |
| 2008/0306359 A1 | 12/2008 | Zdeblick et al. |
| 2008/0306360 A1 | 12/2008 | Robertson et al. |
| 2008/0311852 A1 | 12/2008 | Hansen |
| 2008/0312522 A1 | 12/2008 | Rowlandson |
| 2008/0316020 A1 | 12/2008 | Robertson |

(56) References Cited

U.S. PATENT DOCUMENTS

| | | |
|---|---|---|
| 2009/0009330 A1 | 1/2009 | Sakama et al. |
| 2009/0009332 A1 | 1/2009 | Nunez et al. |
| 2009/0024045 A1 | 1/2009 | Prakash |
| 2009/0024112 A1 | 1/2009 | Edwards et al. |
| 2009/0030293 A1 | 1/2009 | Cooper et al. |
| 2009/0030297 A1 | 1/2009 | Miller |
| 2009/0034209 A1 | 2/2009 | Joo |
| 2009/0043171 A1 | 2/2009 | Rule |
| 2009/0047357 A1 | 2/2009 | Tomohira et al. |
| 2009/0048498 A1 | 2/2009 | Riskey |
| 2009/0062634 A1 | 3/2009 | Say et al. |
| 2009/0062670 A1 | 3/2009 | Sterling |
| 2009/0062730 A1 | 3/2009 | Woo |
| 2009/0069642 A1 | 3/2009 | Gao |
| 2009/0069655 A1 | 3/2009 | Say et al. |
| 2009/0069656 A1 | 3/2009 | Say et al. |
| 2009/0069657 A1 | 3/2009 | Say et al. |
| 2009/0069658 A1 | 3/2009 | Say et al. |
| 2009/0069724 A1 | 3/2009 | Otto et al. |
| 2009/0076343 A1 | 3/2009 | James |
| 2009/0076350 A1 | 3/2009 | Bly et al. |
| 2009/0082645 A1 | 3/2009 | Hafezi et al. |
| 2009/0087483 A1 | 4/2009 | Sison |
| 2009/0088618 A1 | 4/2009 | Ameson |
| 2009/0099435 A1 | 4/2009 | Say et al. |
| 2009/0105561 A1 | 4/2009 | Boydon et al. |
| 2009/0110148 A1 | 4/2009 | Zhang |
| 2009/0112626 A1 | 4/2009 | Talbot |
| 2009/0124871 A1 | 5/2009 | Arshak |
| 2009/0124965 A1 | 5/2009 | Greenberg et al. |
| 2009/0131774 A1 | 5/2009 | Sweitzer |
| 2009/0135886 A1 | 5/2009 | Robertson et al. |
| 2009/0142853 A1 | 6/2009 | Warrington et al. |
| 2009/0149839 A1 | 6/2009 | Hyde et al. |
| 2009/0157113 A1 | 6/2009 | Marcotte |
| 2009/0157358 A1 | 6/2009 | Kim |
| 2009/0161602 A1 | 6/2009 | Matsumoto |
| 2009/0163789 A1 | 6/2009 | Say et al. |
| 2009/0171180 A1 | 7/2009 | Pering |
| 2009/0171420 A1 | 7/2009 | Brown et al. |
| 2009/0173628 A1 | 7/2009 | Say et al. |
| 2009/0177055 A1 | 7/2009 | Say et al. |
| 2009/0177056 A1 | 7/2009 | Say et al. |
| 2009/0177057 A1 | 7/2009 | Say et al. |
| 2009/0177058 A1 | 7/2009 | Say et al. |
| 2009/0177059 A1 | 7/2009 | Say et al. |
| 2009/0177060 A1 | 7/2009 | Say et al. |
| 2009/0177061 A1 | 7/2009 | Say et al. |
| 2009/0177062 A1 | 7/2009 | Say et al. |
| 2009/0177063 A1 | 7/2009 | Say et al. |
| 2009/0177064 A1 | 7/2009 | Say et al. |
| 2009/0177065 A1 | 7/2009 | Say et al. |
| 2009/0177066 A1 | 7/2009 | Say et al. |
| 2009/0182206 A1 | 7/2009 | Najafi |
| 2009/0182207 A1 | 7/2009 | Riskey et al. |
| 2009/0182212 A1 | 7/2009 | Say et al. |
| 2009/0182213 A1 | 7/2009 | Say et al. |
| 2009/0182214 A1 | 7/2009 | Say et al. |
| 2009/0182215 A1 | 7/2009 | Say et al. |
| 2009/0182388 A1 | 7/2009 | Von Arx |
| 2009/0187088 A1 | 7/2009 | Say et al. |
| 2009/0187089 A1 | 7/2009 | Say et al. |
| 2009/0187090 A1 | 7/2009 | Say et al. |
| 2009/0187091 A1 | 7/2009 | Say et al. |
| 2009/0187092 A1 | 7/2009 | Say et al. |
| 2009/0187093 A1 | 7/2009 | Say et al. |
| 2009/0187094 A1 | 7/2009 | Say et al. |
| 2009/0187095 A1 | 7/2009 | Say et al. |
| 2009/0187381 A1 | 7/2009 | King et al. |
| 2009/0192351 A1 | 7/2009 | Nishino |
| 2009/0192368 A1 | 7/2009 | Say et al. |
| 2009/0192369 A1 | 7/2009 | Say et al. |
| 2009/0192370 A1 | 7/2009 | Say et al. |
| 2009/0192371 A1 | 7/2009 | Say et al. |
| 2009/0192372 A1 | 7/2009 | Say et al. |
| 2009/0192373 A1 | 7/2009 | Say et al. |
| 2009/0192374 A1 | 7/2009 | Say et al. |
| 2009/0192375 A1 | 7/2009 | Say et al. |
| 2009/0192376 A1 | 7/2009 | Say et al. |
| 2009/0192377 A1 | 7/2009 | Say et al. |
| 2009/0192378 A1 | 7/2009 | Say et al. |
| 2009/0192379 A1 | 7/2009 | Say et al. |
| 2009/0194747 A1 | 8/2009 | Zou et al. |
| 2009/0197068 A1 | 8/2009 | Yamaguchi et al. |
| 2009/0198115 A1 | 8/2009 | Say et al. |
| 2009/0198116 A1 | 8/2009 | Say et al. |
| 2009/0198175 A1 | 8/2009 | Say et al. |
| 2009/0203964 A1 | 8/2009 | Shimizu et al. |
| 2009/0203971 A1 | 8/2009 | Sciarappa |
| 2009/0203972 A1 | 8/2009 | Heneghan |
| 2009/0203978 A1 | 8/2009 | Say et al. |
| 2009/0204265 A1 | 8/2009 | Hackett |
| 2009/0210164 A1 | 8/2009 | Say et al. |
| 2009/0216101 A1 | 8/2009 | Say et al. |
| 2009/0216102 A1 | 8/2009 | Say et al. |
| 2009/0227204 A1 | 9/2009 | Robertson et al. |
| 2009/0227876 A1 | 9/2009 | Tran |
| 2009/0227940 A1 | 9/2009 | Say et al. |
| 2009/0227941 A1 | 9/2009 | Say et al. |
| 2009/0227988 A1 | 9/2009 | Wood et al. |
| 2009/0228214 A1 | 9/2009 | Say et al. |
| 2009/0231125 A1 | 9/2009 | Baldus |
| 2009/0234200 A1 | 9/2009 | Husheer |
| 2009/0243833 A1 | 10/2009 | Huang |
| 2009/0253960 A1 | 10/2009 | Takenaka et al. |
| 2009/0256702 A1 | 10/2009 | Robertson |
| 2009/0260212 A1 | 10/2009 | Schmett et al. |
| 2009/0264714 A1 | 10/2009 | Chou |
| 2009/0264964 A1 | 10/2009 | Abrahamson |
| 2009/0265186 A1 | 10/2009 | Tarassenko et al. |
| 2009/0273467 A1 | 11/2009 | Elixmann |
| 2009/0281539 A1 | 11/2009 | Selig |
| 2009/0287109 A1 | 11/2009 | Ferren et al. |
| 2009/0295548 A1 | 12/2009 | Ronkka |
| 2009/0296677 A1 | 12/2009 | Mahany |
| 2009/0303920 A1 | 12/2009 | Mahany |
| 2009/0306633 A1 | 12/2009 | Trovato et al. |
| 2009/0312619 A1 | 12/2009 | Say et al. |
| 2009/0318303 A1 | 12/2009 | Delamarche et al. |
| 2009/0318761 A1 | 12/2009 | Rabinovitz |
| 2009/0318779 A1 | 12/2009 | Tran |
| 2009/0318783 A1 | 12/2009 | Rohde |
| 2009/0318793 A1 | 12/2009 | Datta |
| 2010/0001841 A1 | 1/2010 | Cardullo |
| 2010/0010330 A1 | 1/2010 | Rankers |
| 2010/0033324 A1 | 2/2010 | Shimizu et al. |
| 2010/0036269 A1 | 2/2010 | Ferren et al. |
| 2010/0049004 A1 | 2/2010 | Edman et al. |
| 2010/0049006 A1 | 2/2010 | Magar |
| 2010/0049012 A1 | 2/2010 | Dijksman et al. |
| 2010/0049069 A1 | 2/2010 | Tarassenko et al. |
| 2010/0056878 A1 | 3/2010 | Partin |
| 2010/0056891 A1 | 3/2010 | Say et al. |
| 2010/0056939 A1 | 3/2010 | Tarassenko et al. |
| 2010/0057041 A1 | 3/2010 | Hayter |
| 2010/0062709 A1 | 3/2010 | Kato |
| 2010/0063438 A1 | 3/2010 | Bengtsson |
| 2010/0063841 A1 | 3/2010 | D'Ambrosia et al. |
| 2010/0069002 A1 | 3/2010 | Rong |
| 2010/0069717 A1 | 3/2010 | Hafezi et al. |
| 2010/0099967 A1 | 4/2010 | Say et al. |
| 2010/0099968 A1 | 4/2010 | Say et al. |
| 2010/0099969 A1 | 4/2010 | Say et al. |
| 2010/0100077 A1 | 4/2010 | Rush |
| 2010/0100078 A1 | 4/2010 | Say et al. |
| 2010/0106001 A1 | 4/2010 | Say et al. |
| 2010/0118853 A1 | 5/2010 | Godfrey |
| 2010/0139672 A1 | 6/2010 | Kroll et al. |
| 2010/0168659 A1 | 7/2010 | Say et al. |
| 2010/0179398 A1 | 7/2010 | Say et al. |
| 2010/0191073 A1 | 7/2010 | Tarassenko et al. |
| 2010/0210299 A1 | 8/2010 | Gorbachov |
| 2010/0222652 A1 | 9/2010 | Cho |
| 2010/0228113 A1 | 9/2010 | Solosko |

(56) References Cited

U.S. PATENT DOCUMENTS

| | | |
|---|---|---|
| 2010/0233026 A1 | 9/2010 | Ismagliov et al. |
| 2010/0234706 A1 | 9/2010 | Gilland |
| 2010/0234715 A1 | 9/2010 | Shin |
| 2010/0234914 A1 | 9/2010 | Shen |
| 2010/0245091 A1 | 9/2010 | Singh |
| 2010/0249541 A1 | 9/2010 | Geva et al. |
| 2010/0249881 A1 | 9/2010 | Corndorf |
| 2010/0256461 A1 | 10/2010 | Mohamedali |
| 2010/0259543 A1 | 10/2010 | Tarassenko et al. |
| 2010/0268048 A1 | 10/2010 | Say et al. |
| 2010/0268049 A1 | 10/2010 | Say et al. |
| 2010/0268050 A1 | 10/2010 | Say et al. |
| 2010/0274111 A1 | 10/2010 | Say et al. |
| 2010/0280345 A1 | 11/2010 | Say et al. |
| 2010/0280346 A1 | 11/2010 | Say et al. |
| 2010/0295694 A1 | 11/2010 | Kauffman et al. |
| 2010/0297640 A1 | 11/2010 | Kumar et al. |
| 2010/0298650 A1 | 11/2010 | Moon et al. |
| 2010/0298668 A1 | 11/2010 | Hafezi et al. |
| 2010/0298730 A1 | 11/2010 | Tarassenko et al. |
| 2010/0312188 A1 | 12/2010 | Robertson et al. |
| 2010/0312580 A1 | 12/2010 | Tarassenko et al. |
| 2011/0009715 A1 | 1/2011 | O'Reilly et al. |
| 2011/0054265 A1 | 3/2011 | Hafezi et al. |
| 2011/0065983 A1 | 3/2011 | Hafezi et al. |
| 2011/0077660 A1 | 3/2011 | Janik et al. |
| 2011/0124983 A1 | 5/2011 | Kroll et al. |
| 2011/0134906 A1 | 6/2011 | Garudadri et al. |
| 2011/0160549 A1 | 6/2011 | Saroka et al. |
| 2011/0224912 A1 | 9/2011 | Bhavaraju et al. |
| 2011/0230732 A1 | 9/2011 | Edman et al. |
| 2011/0270135 A1 | 11/2011 | Dooley et al. |
| 2012/0004520 A1 | 1/2012 | Whitworth et al. |
| 2012/0011699 A1 | 1/2012 | Hafezi et al. |
| 2012/0016231 A1 | 1/2012 | Westmoreland |
| 2012/0032816 A1 | 2/2012 | Cho et al. |
| 2012/0062371 A1 | 3/2012 | Radivojevic et al. |
| 2012/0071743 A1 | 3/2012 | Todorov et al. |
| 2012/0109112 A1 | 5/2012 | Strand et al. |
| 2012/0179004 A1 | 7/2012 | Roesicke et al. |
| 2012/0245043 A1 | 9/2012 | England |
| 2012/0276451 A1 | 11/2012 | Lestriez et al. |
| 2012/0299723 A1 | 11/2012 | Hafezi et al. |
| 2013/0030366 A1 | 1/2013 | Robertson et al. |
| 2013/0129869 A1 | 5/2013 | Hafezi et al. |
| 2013/0129872 A1 | 5/2013 | Kruger |
| 2013/0144132 A1 | 6/2013 | Hafezi et al. |
| 2013/0171596 A1 | 7/2013 | French |
| 2013/0172690 A1 | 7/2013 | Arne et al. |
| 2013/0185228 A1 | 7/2013 | Dresner |
| 2013/0193950 A1 | 8/2013 | Hafezi et al. |
| 2013/0196012 A1 | 8/2013 | Dill |
| 2013/0199662 A1 | 8/2013 | Gebbink |
| 2013/0209877 A1 | 8/2013 | Kren et al. |
| 2013/0223028 A1 | 8/2013 | Arne et al. |
| 2013/0275296 A1 | 10/2013 | Tietzen et al. |
| 2014/0066734 A1 | 3/2014 | Zdeblick |
| 2014/0179221 A1 | 6/2014 | Whitworth et al. |
| 2014/0180202 A1 | 6/2014 | Zdeblick et al. |
| 2014/0280125 A1 | 9/2014 | Bhardwaj et al. |
| 2014/0308930 A1 | 10/2014 | Tran |
| 2014/0349256 A1 | 11/2014 | Connor |
| 2014/0374276 A1 | 12/2014 | Guthrie et al. |
| 2015/0017486 A1 | 1/2015 | Lai |
| 2015/0059922 A1 | 3/2015 | Thompson et al. |
| 2015/0080677 A1 | 3/2015 | Thompson et al. |
| 2015/0080678 A1 | 3/2015 | Frank et al. |
| 2015/0080679 A1 | 3/2015 | Frank et al. |
| 2015/0080680 A1 | 3/2015 | Zdeblick et al. |
| 2015/0112243 A1 | 4/2015 | Hafezi et al. |
| 2015/0127737 A1 | 5/2015 | Thompson et al. |
| 2015/0127738 A1 | 5/2015 | Thompson et al. |
| 2015/0149375 A1 | 5/2015 | Thompson et al. |
| 2015/0150480 A1 | 6/2015 | Zdeblick et al. |
| 2015/0164746 A1 | 6/2015 | Costello et al. |
| 2015/0173646 A1 | 6/2015 | Berkman et al. |
| 2015/0223751 A1 | 8/2015 | Zdeblick et al. |
| 2015/0230729 A1 | 8/2015 | Zdeblick et al. |
| 2015/0248833 A1 | 9/2015 | Arne et al. |
| 2015/0352343 A1 | 12/2015 | Hafezi et al. |
| 2015/0361234 A1 | 12/2015 | Hafezi et al. |
| 2016/0033667 A1 | 2/2016 | Schmidt et al. |
| 2016/0174900 A1 | 6/2016 | Zdeblick et al. |
| 2016/0345906 A1 | 12/2016 | Johnson et al. |
| 2016/0380708 A1 | 12/2016 | Dua et al. |
| 2017/0000179 A1 | 1/2017 | Cheng et al. |
| 2017/0020182 A1 | 1/2017 | Schmidt et al. |
| 2017/0216569 A1 | 8/2017 | Hafezi et al. |
| 2017/0265813 A1 | 9/2017 | Zdeblick et al. |
| 2017/0274194 A1 | 9/2017 | Robertson et al. |
| 2017/0296799 A1 | 10/2017 | Hafezi et al. |
| 2018/0026680 A1 | 1/2018 | Shirvani et al. |
| 2018/0110441 A1 | 4/2018 | Frank et al. |
| 2018/0184698 A1 | 7/2018 | Arne et al. |
| 2018/0214048 A1 | 8/2018 | Zdeblick et al. |
| 2018/0229996 A1 | 8/2018 | Thompson |

FOREIGN PATENT DOCUMENTS

| | | |
|---|---|---|
| CN | 101795202 | 8/2010 |
| DE | 10313005 | 10/2004 |
| EP | 0344939 | 12/1989 |
| EP | 0526166 | 2/1993 |
| EP | 0981152 | 2/2000 |
| EP | 1246356 | 10/2002 |
| EP | 1534054 | 5/2005 |
| EP | 1702553 | 9/2006 |
| EP | 1244308 | 12/2007 |
| EP | 2143369 | 1/2010 |
| GB | 827762 | 2/1960 |
| JP | 61072712 | 4/1986 |
| JP | H01285247 | 11/1989 |
| JP | 05228128 | 9/1993 |
| JP | H11195415 | 7/1999 |
| JP | 2000506410 | 5/2000 |
| JP | 2002263185 | 9/2002 |
| JP | 2002282219 | 10/2002 |
| JP | 2003050867 | 2/2003 |
| JP | 2004313242 | 11/2004 |
| JP | 2005073886 | 3/2005 |
| JP | 2005087552 | 4/2005 |
| JP | 2005102959 | 4/2005 |
| JP | 2005304880 | 4/2005 |
| JP | 2005124708 | 5/2005 |
| JP | 2005514966 | 5/2005 |
| JP | 2005343515 | 12/2005 |
| JP | 20055332328 | 12/2005 |
| JP | 2006006377 | 1/2006 |
| JP | 2006509574 | 3/2006 |
| JP | 2007200739 | 8/2007 |
| JP | 2007313340 | 12/2007 |
| JP | 2009514870 | 4/2009 |
| JP | 2009528909 | 8/2009 |
| KR | 200600977523 | 7/2006 |
| TW | 200406192 | 5/2004 |
| TW | 200916136 | 4/2009 |
| WO | WO1988002237 | 4/1988 |
| WO | WO1992021307 | 12/1992 |
| WO | WO1993008734 | 5/1993 |
| WO | WO1993019667 | 10/1993 |
| WO | WO1994001165 | 1/1994 |
| WO | WO1997039963 | 10/1997 |
| WO | WO1998043537 | 10/1998 |
| WO | WO1999037290 | 7/1999 |
| WO | WO1999059465 | 11/1999 |
| WO | WO2001000085 | 1/2000 |
| WO | WO2000032474 | 6/2000 |
| WO | WO2000033246 | 6/2000 |
| WO | WO2001047466 | 7/2001 |
| WO | WO2001058236 | 8/2001 |
| WO | WO2001074011 | 10/2001 |
| WO | WO2001080731 | 11/2001 |
| WO | WO2002000920 | 1/2002 |
| WO | WO2002045489 | 6/2002 |

(56) References Cited

FOREIGN PATENT DOCUMENTS

| | | |
|---|---|---|
| WO | WO2002058330 | 7/2002 |
| WO | WO2002062276 | 8/2002 |
| WO | WO2002087681 | 11/2002 |
| WO | WO2002095351 | 11/2002 |
| WO | WO2003005877 | 1/2003 |
| WO | WO2003050643 | 6/2003 |
| WO | WO2003068061 | 8/2003 |
| WO | WO2004014225 | 2/2004 |
| WO | WO2004019172 | 3/2004 |
| WO | WO2004039256 | 5/2004 |
| WO | WO2004066833 | 8/2004 |
| WO | WO2004066834 | 8/2004 |
| WO | WO2004066903 | 8/2004 |
| WO | WO2004068881 | 8/2004 |
| WO | WO2004075032 | 9/2004 |
| WO | WO2004109316 | 12/2004 |
| WO | WO2005011237 | 2/2005 |
| WO | WO2005020023 | 3/2005 |
| WO | WO2005024687 | 3/2005 |
| WO | WO2005041438 | 5/2005 |
| WO | WO2005047837 | 5/2005 |
| WO | WO2005051166 | 6/2005 |
| WO | WO2005053517 | 6/2005 |
| WO | WO2005083621 | 9/2005 |
| WO | WO2005110238 | 11/2005 |
| WO | WO2005123569 | 12/2005 |
| WO | WO2006021932 | 3/2006 |
| WO | WO2006027586 | 3/2006 |
| WO | WO2006028347 | 3/2006 |
| WO | WO2006055892 | 5/2006 |
| WO | WO2006055956 | 5/2006 |
| WO | WO2006075016 | 7/2006 |
| WO | WO2006100620 | 9/2006 |
| WO | WO2006104843 | 10/2006 |
| WO | WO2006116718 | 11/2006 |
| WO | WO2006127355 | 11/2006 |
| WO | WO2007001724 | 1/2007 |
| WO | WO2007001742 | 1/2007 |
| WO | WO2007013952 | 2/2007 |
| WO | WO2007014084 | 2/2007 |
| WO | WO2007014527 | 2/2007 |
| WO | WO2007021496 | 2/2007 |
| WO | WO2007027660 | 3/2007 |
| WO | WO2007028035 | 3/2007 |
| WO | WO2007036687 | 4/2007 |
| WO | WO2007036741 | 4/2007 |
| WO | WO2007036746 | 4/2007 |
| WO | WO2007040878 | 4/2007 |
| WO | WO2007067054 | 6/2007 |
| WO | WO2007071180 | 6/2007 |
| WO | WO2007096810 | 8/2007 |
| WO | WO2007101141 | 9/2007 |
| WO | WO2007115087 | 10/2007 |
| WO | WO2007120946 | 10/2007 |
| WO | WO2007127316 | 11/2007 |
| WO | WO2007127879 | 11/2007 |
| WO | WO2007128165 | 11/2007 |
| WO | WO2007130491 | 11/2007 |
| WO | WO2007143535 | 12/2007 |
| WO | WO2007149546 | 12/2007 |
| WO | WO2008008281 | 1/2008 |
| WO | WO2008012700 | 1/2008 |
| WO | WO2008030482 | 3/2008 |
| WO | WO2008052136 | 5/2008 |
| WO | WO2008063626 | 5/2008 |
| WO | WO2008066617 | 6/2008 |
| WO | WO2008076464 | 6/2008 |
| WO | WO2008089232 | 7/2008 |
| WO | WO2008091683 | 7/2008 |
| WO | WO2008095183 | 8/2008 |
| WO | WO2008097652 | 8/2008 |
| WO | WO2008101107 | 8/2008 |
| WO | WO2008112577 | 9/2008 |
| WO | WO2008112578 | 9/2008 |
| WO | WO2008120156 | 10/2008 |
| WO | WO2008133394 | 11/2008 |
| WO | WO2008134185 | 11/2008 |
| WO | WO2008150633 | 12/2008 |
| WO | WO2009000447 | 12/2008 |
| WO | WO2009001108 | 12/2008 |
| WO | WO2009006615 | 1/2009 |
| WO | WO2009029453 | 3/2009 |
| WO | WO2009031149 | 3/2009 |
| WO | WO2009036334 | 3/2009 |
| WO | WO2009051829 | 4/2009 |
| WO | WO2009051830 | 4/2009 |
| WO | WO2009063377 | 5/2009 |
| WO | WO2009081348 | 7/2009 |
| WO | WO2009111664 | 9/2009 |
| WO | WO2009146082 | 12/2009 |
| WO | WO2010009100 | 1/2010 |
| WO | WO2010011833 | 1/2010 |
| WO | WO2010019778 | 2/2010 |
| WO | WO2010057049 | 5/2010 |
| WO | WO2010080765 | 7/2010 |
| WO | WO2010080843 | 7/2010 |
| WO | WO2010107563 | 9/2010 |
| WO | WO2010129288 | 11/2010 |
| WO | WO2010132331 | 11/2010 |
| WO | WO2010135516 | 11/2010 |
| WO | WO2011068963 | 6/2011 |
| WO | WO2011133799 | 10/2011 |
| WO | WO2011159336 | 12/2011 |
| WO | WO2011159337 | 12/2011 |
| WO | WO2011159338 | 12/2011 |
| WO | WO2011159339 | 12/2011 |
| WO | WO2012/112561 | 8/2012 |
| WO | WO2015112603 | 7/2015 |
| WO | WO2015112604 | 7/2015 |
| WO | WO2015119911 | 8/2015 |

OTHER PUBLICATIONS

Arshak et al., A Review and Adaptation of Methods of Object Tracking to Telemetry Capsules IC-Med (2007) vol. 1, No. 1, Issue 1, 12pp.

"ASGE Technology Status Evaluation Report: wireless capsule endoscopy" American Soc. for Gastrointestinal Endoscopy (2006) vol. 63, No. 4; 7 pp.

Au-Yeung, K., et al., "A Networked System for Self-Management of Drug Therapy and Wellness", Wireless Health '10, Oct. 5-7, 2010, San Diego, 9 pages.

Aydin et al., "Design and implementation considerations for an advanced wireless interface in miniaturized integrated sensor Microsystems" Sch. of Eng. & Electron., Edinburgh Univ., UK; (2003); abstract.

Bohidar et al., "Dielectric Behavior of Gelatin Solutions and Gels" Colloid Polym Sci (1998) 276:81-86.

Carlson et al., "Evaluation of a non-invasive respiratory monitoring system for sleeping subjects" Physiological Measurement (1999) 20(1): 53.

Coury, L. "Conductance Measurement Part 1: Theory"; Current Separations, 18:3 (1999) p. 91-96.

Delvaux et al., "Capsule endoscopy: Technique and indications" Clinical Gastroenterology (2008) vol. 22, Issue 5, pp. 813-837.

Dhar et al., "Electroless nickel plated contacts on porous silicon" Appl. Phys. Lett. 68 (10) pp. 1392-1393 (1996).

Eldek A., "Design of double dipole antenna with enhanced usable bandwidth for wideband phased array applications" Progress in Electromagnetics Research PIER 59, 1-15 (2006).

Ferguson et al., "Dielectric Constant Studies III Aqueous Gelatin Solutions" J. Chem. Phys. 2, 94 (1934) p. 94-98.

Furse C. M., "Dipole Antennas" J. Webster (ed). Wiley Encyclopedia of Electrical and Electronics Engineering (1999) p. 575-581.

Gaglani S. "Put Your Phone, or Skin, on Vibrate" MedGadget (2012) http://medgadget.com/2012/03/put-your-phone-or-skin-on-vibrate.html 8pp.

Gilson, D.R. "Molecular dynamics simulation of dipole interactions", Department of Physics, Hull University, Dec. 2002, p. 1-43.

(56) References Cited

OTHER PUBLICATIONS

Given Imaging, "Agile Patency Brochure" (2006) http://www.inclino.no/documents/AgilePatencyBrochure_Global_GMB-0118-01.pdf; 4pp.
Gonzalez-Guillaumin et al., "Ingestible capsule for impedance and pH monitoring in the esophagus" IEEE Trans Biomed Eng. (2007) 54(12): 2231-6; abstract.
Greene, "Edible RFID microchip monitor can tell if you take your medicine" Bloomberg Businessweek (2010) 2 pp.; http://www.businessweek.com/idg/2010-03-31/edible-rfid-microchip-monitor-can-tell-if-you-take-your-medicine.html.
Heydari et al., "Analysis of the PLL jitter due to power/ground and substrate noise"; IEEE Transactions on Circuits and Systems (2004) 51(12): 2404-16.
Hoover et al., "Rx for health: Engineers design pill that signals it has been swallowed" University of Florida News (2010) 2pp.; http://news.ufl.edu/2010/03/31/antenna-pill-2/.
INTROMEDIC, MicroCam Innovative Capsule Endoscope Pamphlet. (2006) 8 pp (http://www.intromedic.com/en/product/productinfo.asp).
ISFET—Ion Sensitive Field-Effect Transistor; Microsens S.A. pdf document. Office Action dated Jun. 13, 2011 for U.S. Appl. No. 12/238,345; 4pp.
Jung, S. "Dissolvable 'Transient Electronics' Will Be Good for Your Body and the Environment" MedGadget; Oct. 1, 2012; Onlne website: http://medgadget.com/2012/10/dissolvable-transient-electronics-will-be-good-for-your-body-and-the-environment.html; downloaded Oct. 24, 2012; 4 pp.
Juvenile Diabetes Research Foundation International (JDRF), "Artificial Pancreas Project" (2010); http://www.artificialpancreasproject.com/; 3 pp.
Kamada K., "Electrophoretic deposition assisted by soluble anode" Materials Letters 57 (2003) 2348-2351.
Kendle, Earl R. and Morris, Larry A., "Preliminary Studies in the Development of a Gastric Battery for Fish" (1964). Nebraska Game and Parks Commission White Papers, Conference Presentations, & Manuscripts. Paper 22. p. 1-6.
Kim et al., "A Semi-Interpenetrating Network System for a Polymer Membrane"; Eur. Polym. J. vol. 33 No. 7; pp. 1009-1014 (1997).
Li, P-Y, et al. "An electrochemical intraocular drug delivery device", Sensors and Actuators A 143 (2008) p. 41-48.
LIFESCAN, "OneTouch UltraLink™"http://www.lifescan.com/products/meters/ultralink (2010) 2 pp.
MacKay et al., "Radio Telemetering from within the Body" Inside Information is Revealed by Tiny Transmitters that can be Swallowed or Implanted in Man or Animal Science (1991) 1196-1202; 134; American Association for the Advancement of Science, Washington D.C.
MacKay et al., "Endoradiosonde" Nature, (1957) 1239-1240, 179 Nature Publishing Group.
McKenzie et al., "Validation of a new telemetric core temperature monitor" J. Therm. Biol. (2004) 29(7-8):605-11.
MEDTRONIC, "CareLink Therapy Management Software for Diabetes" (2010); https://carelink.minimed.com/patient/entry.jsp?bhcp=1; 1 pp.
MEDTRONIC, "Carelink™ USB" (2008) http://www.medtronicdiabetes.com/pdf/carelink_usb_factsheet.pdf 2pp.
MEDTRONIC "The New MiniMed Paradigm® Real-Time Revel™ System" (2010) http://www.medtronicdiabetes.com/products/index.html; 2 pp.
MEDTRONIC, "Mini Med Paradigm® Revel™ Insulin Pump" (2010) http://www.medtronicdiabetes.com/products/insulinpumps/index.html; 2 pp.
MEDTRONIC, Mini Med Paradigm™ Veo™ System: Factsheet (2010). http://www.medtronic-diabetes.com.au/downloads/Paradigm%20Veo%20Factsheet.pdf ; 4 pp.
Mojaverian et al., "Estimation of gastric residence time of the Heidelberg capsule in humans: effect of varying food composition" Gastroenterology (1985) 89:(2): 392-7.

O'Brien et al., "The Production and Characterization of Chemically Reactive Porous Coatings of Zirconium Via Unbalanced Magnetron Sputtering" Surface and Coatings Technology (1996) 86-87; 200-206.
Park, "Medtronic to Buy MiniMed for $3.7 Billion" (2001) HomeCare; http://homecaremag.com/mag/medical_medtronic_buy_minimed/; 2 pp.
Radio Antennae, http://www.erikdeman.de/html/sail018h.htm; (2008) 5 pages.
Rolison et al., "Electrically conductive oxide aerogels: new materials in electrochemistry" J. Mater. Chem. (2001) 1, 963-980.
Roulstone, et al., "Studies on Polymer Latex Films: I. A study of latex film morphology" Polymer International 24 (1991) pp. 87-94.
Sanduleanu et al., "Octave tunable, highly linear, RC-ring oscillator with differential fine-coarse tuning, quadrature outputs and amplitude control for fiber optic transceivers" (2002) IEEE MTT-S International Microwave Symposium Digest 545-8.
Santini, J.T. et al, "Microchips as controlled drug delivery-devices", Agnew. Chem. Int. Ed. (2000), vol. 39, p. 2396-2407.
"SensiVida minimally invasive clinical systems" Investor Presentation Oct. 2009 28pp; http://www.sensividamedtech.com/SensiVidaGeneralOctober09.pdf.
Shawgo, R.S. et al. "BioMEMS from drug delivery", Current Opinion in Solid State and Material Science 6 (2002), p. 329-334.
Shin et al., "A Simple Route to Metal Nanodots and Nanoporous Metal Films"; Nano Letters, vol. 2, No. 9 (2002) pp. 933-936.
"Smartlife awarded patent for knitted transducer" Innovation in Textiles News: http://www.innovationintextiles.com/articles/208.php; 2pp. (2009).
Solanas et al., "RFID Technology for the Health Care Sector" Recent Patents on Electrical Engineering (2008) 1, 22-31.
Soper, S.A. et al. "Bio-Mems Technologies and Applications", Chapter 12, "MEMS for Drug Delivery", p. 325-346 (2007).
Swedberg, "University Team Sees Ingestible RFID Tag as a Boon to Clinical Trials" RFID Journal Apr. 27, 2010; http://www.rfidjournal.com/article/view/7560/1 3pp.
Tajalli et al., "Improving the power-delay performance in subthreshold source-coupled logic circuits" Integrated Circuit and System Design. Power and Timing Modeling, Optimization and Simulation, Springer Berlin Heidelberg (2008) 21-30.
Tatbul et al., "Confidence-based data management for personal area sensor networks" ACM International Conference Proceeding Series (2004) 72.
Tierney, M.J. et al "Electroreleasing Composite Membranes for Delivery of Insulin and other Biomacromolecules", J. Electrochem. Soc., vol. 137, No. 6, Jun. 1990, p. 2005-2006.
Trutag Technologies, Inc., Spectral Microtags for Authentication and Anti-Counterfeiting; "Product Authentication and Brand Protection Solutions"; http://www.trutags.com/; downloaded Feb. 12, 2013; 1 pp.
Walkey, "MOSFET Structure and Processing"; 97.398* Physical Electronics Lecture 20; 24 pp.
Wang, X. et al "Resistance to Tracking and Erosion of Silicone Rubber Material under Various Types of Precipitation", Jpn. J. Appl. Phys. vol. 38 (1999) pp. 5170-5175.
Watson, et al., "Determination of the relationship between the pH and conductivity of gastric juice" Physiol Meas. 17 (1996) pp. 21-27.
Winter, J. et al. "The material properties of gelatin gels"; USA Ballistic Research Laboratories, Mar. 1975, p. 1-157.
Wongmanerod et al., "Determination of pore size distribution and surface area of thin porous silicon layers by spectroscopic ellipsometry" Applied Surface Science 172 (2001) 117-125.
Xiaoming et al., "A telemedicine system for wireless home healthcare based on bluetooth and the internet" Telemedicine Journal and e-health (2004) 10(S2): S110-6.
Yang et al., "Fast-switching frequency synthesizer with a discriminator-aided phase detector" IEEE Journal of Solid-State Circuits (2000) 35(10): 1445-52.
Zimmerman, "Personal Area Networks: Near-field intrabody communication" IBM Systems Journal (1996) 35 (3-4):609-17.
Zworkin, "A Radio Pill" Nature, (1957) 898, 179 Nature Publishing Group.

(56) References Cited

OTHER PUBLICATIONS

Target Innovations, Tablet Metal Detector, https ://web. arch ive. org/web/20 130215063351/http://www. metaldetectorindia.com/ tablet -metal-detector. html, Feb. 15, 2013, 2 pg.
TargetPharmaceutical Metal Detector, Feb. 15, 2013 downloaded from Target Innovations, Tablet Metal Detector, Feb. 15, 2013, 1 pg.
Youtube video Pharmaceutical Metal Detector/Tablet Metal Detector/ Capsule Metal Detector/ Dry Fruits; https://www.youtube.com/watch?v=l0126txam_s, May 12, 2012.

* cited by examiner

HIGHLY RELIABLE INGESTIBLE EVENT MARKERS AND METHODS FOR USING THE SAME

CROSS-REFERENCE TO RELATED APPLICATIONS

This application is a continuation of U.S. patent application Ser. No. 13/756,280, filed on Jan. 31, 2013, entitled "HIGHLY RELIABLE INGESTIBLE EVENT MARKERS AND METHODS FOR USING THE SAME", now U.S. Pat. No. 9,320,455, which application is a continuation of U.S. patent application Ser. No. 12/744,642, filed on May 25, 2010, entitled "HIGHLY RELIABLE INGESTIBLE EVENT MARKERS AND METHODS FOR USING THE SAME" now U.S. Pat. No. 8,545,402, which application is a 371 application of International Application No. PCT/US2010/032590, filed on Apr. 27, 2010, and which application, pursuant to 35 U.S.C. § 119 (e), claims priority to the filing date of U.S. Provisional Patent Application Ser. No. 61/173,511 filed Apr. 28, 2009 and to the filing date of U.S. Provisional Patent Application Ser. No. 61/173,564 filed Apr. 28, 2009; the disclosure of which applications are herein incorporated by reference.

INTRODUCTION

There are many instances in both medical and non-medical applications where one desires to note a personal event, i.e., an event that is specific to a given individual. Examples of medical applications where one may wish to note an event that is specific to a given individual include, but are not limited to, the onset of one or more physiological parameters of interest, including disease symptoms, the administration of a medication, etc. Examples of non-medical applications where one desires to note an event that is specific to a given individual include, but are not limited to: the ingestion of certain types of foods, e.g., for individuals on controlled diets, the commencement of an exercise regimen, etc.

Because there are many instances where one wishes to note a personal event, a variety of different methods and technologies have been developed to make such notation possible. For example, log books and techniques have been developed in which individuals, e.g., patients and/or their health care provides, can record, e.g., by manually writing or data entry, time and date of an event.

However, there continues to be a need for improvements in personal event monitoring. For example, manually logging when an event takes place can be time consuming and prone to error.

SUMMARY

Event markers, e.g., ingestible event markers, having high reliability are provided. Aspects of the event markers include a support, a control circuit physically associated with the support to control the highly reliable event marker, a first electrochemical material physically associated with the support and electrically coupled to the control circuit, a second electrochemical material electrically coupled to the control circuit and physically associated with the support at a location different from the location of the first material, such that the first and second electrochemical materials are electrically isolated from each other; and a membrane physically associated to the support and positioned relative to the first electrochemical and second electrochemical materials to generate a virtual dipole length larger than an actual dipole length defined by the first and the second electrochemical materials.

DETAILED DESCRIPTION

Figure 1A:
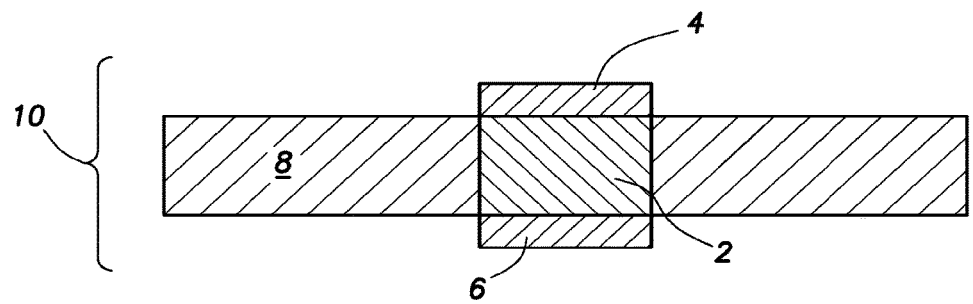
FIGS. 1A to 1F provide views of various IEM configurations according to different aspects of the invention.

Event markers, e.g., ingestible event markers ("IEMs", sometimes referred to herein as "identifiers"), having high reliability are provided. Aspects of the ingestible event markers include a support, a control circuit physically associated with the support to control the highly reliable event marker, a first electrochemical material physically associated with the support and electrically coupled to the control circuit, a second electrochemical material electrically coupled to the control circuit and physically associated with the support at a location different from the location of the first material, such that the first and second electrochemical materials are electrically isolated from each other; and a membrane physically associated to the support and positioned relative to the first electrochemical and second electrochemical materials to generate a virtual dipole length larger than an actual dipole length defined by the first and the second electrochemical materials.

Ingestible Event Markers

As summarized above, ingestible event markers (IEMs) of the invention are highly reliable. By "highly reliable" is meant that the ingestible event markers of the invention correctly generate and transmit a signal when employed in an application for which they are intended at a frequency of 80% or greater, such as 90% or greater, including 95% or greater. Highly reliable ingestible event markers of the invention may correctly generate and transmit a signal at a frequency of 99.5% or greater, such as 99.9% or greater, and in some instances correctly generate and transmit a signal at a frequency of 100%. As further developed below, the highly reliable characteristic of the ingestible event markers may arise from one or more components and/or structural features of the IEM, as described in greater detail below. As reviewed in greater detail below, one or more components and/or structural features of the IEM may impart to the IEM one or more of the following characteristics: enhanced signal strength, extended lifetime, enhanced wetting by stomach fluid, reduced propensity for blockage by GI lining, reduced propensity of blockage by bubbles and/or antifoaming, reduced propensity for floating, as compared to a suitable control. These desirable characteristics may be imparted to a given IEM by one or more structural features and/or chemical constituents, as reviewed in greater detail below.

An ingestible event marker is a device that is dimensioned to be ingestible and includes an IEM made up of an IEM circuitry component and a membrane. The IEM may also include a vehicle. A pharmaceutically active agent may be present in the membrane and/or vehicle. As the IEMs are dimensioned to be ingestible, in certain instances they are sized so that they can be placed in a human mouth and swallowed. In some instances, IEMs of the invention have a longest dimension that is 30 mm or less, such as 20 mm or less, including 5 mm or less.

Various aspects of event markers, e.g., ingestible event markers, of interest are described in PCT application serial no. PCT/US2006/016370 published as WO/2006/116718; PCT application serial no. PCT/US2007/082563 published as WO/2008/052136; PCT application serial no. PCT/US2007/024225 published as WO/2008/063626; PCT application serial no. PCT/US2007/022257 published as WO/2008/066617; PCT application serial no. PCT/US2008/052845 published as WO/2008/095183; PCT application serial no. PCT/US2008/053999 published as WO/2008/101107; PCT application serial no. PCT/US2008/056296 published as WO/2008/112577; PCT application serial no. PCT/US2008/056299 published as WO/2008/112578; and PCT application serial no. PCT/US2008/077753 published as WO2009/042812; the disclosures of which are herein incorporated by reference. In certain aspects, the ingestible event markers are disrupted upon administration to a subject. As such, in certain aspects, the compositions are physically broken, e.g., dissolved, degraded, eroded, etc., following delivery to a body, e.g., via ingestion, injection, etc. The compositions of these aspects are distinguished from devices that are configured to be ingested and survive transit through the gastrointestinal tract substantially, if not completely, intact.

Highly Reliable Event Marker

In various aspects, the highly reliable event marker includes a support, a control circuit physically associated with the support to control the highly reliable event marker, a first electrochemical material physically associated with the support and electrically coupled to the control circuit, a second electrochemical material electrically coupled to the control circuit and physically associated with the support at a location different from the location of the first material, such that the first and second electrochemical materials are electrically isolated from each other; and a membrane physically associated to the support and positioned relative to the first electrochemical and second electrochemical materials to generate a virtual dipole length larger than an actual dipole length defined by the first and the second electrochemical materials.

The highly reliable event marker may be configured to be activated upon contact with fluid at the target site, such as a conducting fluid, e.g., a stomach fluid, providing, for example, a voltage potential difference. In various aspects, the control circuit controls the conductance through logic that alters the overall impedance of the system. The control circuit, for example, may be electrically coupled to a clock. The clock may provide a clock cycle to the control circuit. Based upon the programmed characteristics of the control circuit, when a set number of clock cycles have passed, the control circuit alters the conductance characteristics between electrochemical materials. This cycle may be repeated and thereby the control circuit may produce a unique current signature characteristic, sometimes referred to herein as a "current signature". The control circuit may also be electrically coupled to a memory. Both the clock and the memory may be powered by the voltage potential created between the materials when in contact with a conducting fluid.

With respect to current signatures, the current signatures may distinguish one class of highly reliable event marker from other types or may be universally unique, such as where the current signature is analogous to a human fingerprint which is distinct from any other fingerprint of any other individual and therefore uniquely identifies an individual on a universal level. In various aspects, the control circuit may generate a variety of different types of communications, including but not limited to: RF signals, magnetic signals, conductive (near field) signals, acoustic signals, etc.

Receivers, as heretofore described in various aspects of the present invention, do not require any additional cable or hard wire connection between the device and a receiver of the communication, sometimes referred to herein as a detector.

In some instances, the highly reliable event marker includes two dissimilar electrochemical materials which serve as a cathode and an anode. When the two dissimilar electrochemical materials come in contact with the body fluid, such as stomach fluid, a potential difference (voltage) is generated between the cathode and the anode as a result of the respective oxidation and reduction reactions occurring at the two dissimilar electrochemical materials. The dissimilar electrochemical materials making up the electrochemical materials can be made of any two materials appropriate to the environment in which the IEM circuitry component will be operating. The active materials are any pair of materials with different electrochemical potentials. The electrochemical material materials may be chosen to provide for a voltage upon contact with the target physiological site that is sufficient to drive a signal generation element of the IEM circuitry component. Where desired, the voltage provided by the two dissimilar electrochemical materials upon contact of the metals of the power source with the target physiological site is 0.001 V or higher, including 0.01 V or higher, such as 0.1 V or higher, e.g., 0.3 V or higher, including 0.5 volts or higher, and including 1.0 volts or higher, where in certain aspects, the voltage ranges from about 0.001 to about 10 volts, such as from about 0.01 to about 10 V.

Anode materials of interest include, but are not limited to: magnesium, zinc, sodium, lithium, iron and alloys thereof, e.g., Al and Zn alloys of Mg, which may or may not be intercalated with a variety of materials such, as graphite with Li, K, Ca, Na, Mg, and the like. Cathode materials of interest include, but are not limited to, copper salts, such as copper salts of iodide, chloride, bromide, sulfate, formate, $Fe^{3+}$ salts, e.g., orthophosphate, pyrophosphate, etc. One or both of the metals may be doped with a non-metal, for example to enhance the voltage output of a partial power source or a battery. Non-metals that may be used as doping agents in certain aspects include, but are not limited to: sulfur, iodine and the like. In certain aspects, the electrochemical material materials are cuprous iodine (CuI) or cuprous chloride (CuCl) as the anode and magnesium (Mg) metal or magnesium alloy as the cathode. Aspects of the present invention use electrochemical material materials that are not harmful to the human body. When the materials are exposed and come into contact with the body fluid, such as stomach acid or other types of fluid (either alone or in combination with a dried conductive medium precursor), a potential difference, that is, a voltage, is generated between the electrochemical materials as a result of the respective oxidation and reduction reactions incurred to the two electrochemical material materials. A voltaic cell, or battery, can thereby be produced. Accordingly, in embodiments of the invention, such power supplies are configured such that when the two dissimilar materials are exposed to the target site, e.g., the stomach, the digestive tract, etc., a voltage is generated.

Electrochemical material materials of interest include those that generate substantially little, if any, gaseous bubbles upon contact with an aqueous physiological fluid, such as stomach acid. Electrochemical material materials of interest include metal alloys, where alloys of interest include, but are not limited to, alloys of Mg, Zn, Al, and Li. When present, the amount of metal alloy may range from 0.01 to 15, such as 0.1 to 15 including 1 to 15% by weight. One or more different alloy elements may be present in the alloy. Of interest in some aspects are "bubble-free" Mg alloys which are MgAl or MgZn alloys, such as but not limited to: AZ31 magnesium alloy, AZ61 magnesium alloy, and the like.

Highly reliable event markers, e.g., IEMs, may include a solid support. In certain aspects, the solid support is small, e.g., where it is dimensioned to have a width ranging from about 0.01 mm to about 20 mm, e.g., from about 0.1 mm to about 10 mm, including from about 0.5 mm to about 2 mm; a length ranging from about 0.01 mm to about 20 mm, e.g., from about 0.1 mm to about 20 mm, including from about 0.5 mm to about 2 mm, and a height ranging from about 0.01 mm to about 10 mm, e.g., from about 0.05 mm to about 2 mm, including from about 0.1 mm to about 0.5 mm. The solid support element may take a variety of different configurations, such as but not limited to: a chip configuration, a cylinder configuration, a spherical configuration, a disc configuration, etc, where a particular configuration may be selected based on intended application, method of manufacture, etc. While the material from which the solid support is fabricated may vary considerably, in certain aspects the solid support is made up of a semiconductor material, e.g., silicon.

The phrase "single integrated circuit" refers to a single circuit structure that includes all of the different desired functional blocks for the device. In these aspects, the integrated circuit is a monolithic integrated circuit (also known as IC, microcircuit, microchip, silicon chip, computer chip or chip) that is a miniaturized electronic circuit (which may include semiconductor devices, as well as passive components) that has been manufactured in the surface of a thin substrate of semiconductor material. The integrated circuits of certain aspects of the present invention may be hybrid integrated circuits, which are miniaturized electronic circuits constructed of individual semiconductor devices, as well as passive components, bonded to a substrate or circuit board.

IEMs may be fabricated using any convenient protocol. IEM fabrication protocols of interest include, but are not limited to, those described in PCT application serial no. PCT/US2006/016370 published as WO/2006/116718; PCT application serial no. PCT/US2007/082563 published as WO/2008/052136; PCT application serial no. PCT/US2007/024225 published as WO/2008/063626; PCT application serial no. PCT/US2007/022257 published as WO/2008/066617; PCT application serial no. PCT/US2008/052845 published as WO/2008/095183; PCT application serial no. PCT/US2008/053999 published as WO/2008/101107; PCT application serial no. PCT/US2008/056296 published as WO/2008/112577; PCT application serial no. PCT/US2008/056299 published as WO/2008/112578; and PCT application serial no. PCT/US2008/077753, the disclosures of which are herein incorporated by reference.

A given IEM may include a single IEM, or two or more IEMs, such as three or more, four or more, five or more, six or more, seven or more, eight or more, nine or more, or ten or more IEMs.

In some instances, an IEM may include a swellable or water-absorbing coating that serves to control the microenvironment of the IEM in a desired manner. Of interest in certain instances as swellable coatings are hydrogel coatings. Hydrogel coatings are polymeric coatings made up of one or more different types of non-water soluble polymers, where the coatings absorb water upon contact with an aqueous medium to produce a hydrated gel-structure that has a high water content, such as 90% or more w/w, including 95% or more w/w, such as 99% or more w/w. Any physiologically acceptable hydrogel composition may be employed as a coating, where hydrogel compositions of interest may include one or more of the following polymers: polyethylene oxides, acetates, etc. In some instances, the hydrogel coating may include one or more agents which provide for a controlled environment (for example in terms of conductivity or pH) when the ingestible event marker reaches the target physiological site. Agents of interest include, but are not limited to: salts of physiologically acceptable electrolytes, such as but not limited to: sodium ion, chloride ion, potassium ion and calcium ion, magnesium ion, etc. Specific physiologically compatible salts of interest include, but are not limited to: KCl, NaCl, $MgCl_2$, and the like. Desired pH may range from 1 to 8, such as 2 to 7, and may be imparted by the presence of any suitable buffering agent.

Coatings may take a variety of different configurations, such as layers, snap-fit pre-made capsule components, etc. When present, coatings may cover only a portion of the ingestible event marker envelope the entire device. The coating may be uniform in terms of thickness.

Membrane

IEMs may include at least a pair of signal transmission elements, e.g., in the form of first and second electrochemical materials, which have an actual dipole length. Also present is a membrane which, for example, produces a virtual dipole length between the pair of transmission elements that is larger than the actual dipole length. In addition to controlling the magnitude of the current path between the materials, a membrane (sometimes referred to herein as "amplifier") is used to increase the "length" of the current path and, hence, act to boost the conductance path, as disclosed in the U.S. patent application Ser. No. 12/238,345 entitled, "In-Body Device with Virtual Dipole Signal Amplification" filed Sep. 25, 2008, and in the U.S. patent application Ser. No. 12/564,017 entitled, "Communication System with Partial Power Source" filed Sep. 21, 2009 the entire content of which are incorporated herein by reference. Alternatively, throughout the disclosure herein, the terms "membrane", and "amplifier" are interchangeably with the term "current path extender" without impacting the scope or the present aspects and the claims herein. While the length of the virtual dipole provided by the membrane may vary, in certain instances the length of the virtual dipole is two or more times, such as three or more times, e.g., five or more times, twenty or more times, etc., longer than the length of the actual dipole that exists between the pair of transmission elements. As the length of an actual dipole in a given IEM may vary, ranging in certain instances from 100 µm to 2 cm, such as 300 µm to 1 mm, the length of the virtual dipole may range, in certain instances, from 200 µm to 20 cm, such as 600 µm to 20 mm. In addition to the IEMs of the invention further include a membrane, where the membrane includes a pharmaceutically active agent.

The membrane may have a variety of different configurations, so long as it serves to provide a virtual dipole having a length that is longer than that of the actual dipole length between two or more of, such as a pair of, of signal transmission elements. In certain aspects, the membrane is a structure that is positioned between the pair of signal transmission elements. The membrane may have a two-dimensional or three-dimensional configuration, and may have any convenient shape, such as square, disc, triangular, ovoid, irregular, etc., as developed in greater detail below. The length of the virtual dipole provided by the signal amplification element is, in certain instances, dependent on the particular shape of the signal amplification element. For example, where the signal amplification element has a disc configuration, as developed in greater detail below, the length of the virtual dipole is substantially the same as, if not identical to, the radius of the disc.

The pair of transmission elements are, in certain instances, a pair of electrochemical materials positioned on opposing sides of a solid support, e.g., where the solid support comprises an integrated circuit. For example, where the integrated circuit has an upper electrochemical material and lower electrochemical material on opposing sides or surfaces of an integrated circuit, the membrane may be an insulative material (or composite material) positioned between the upper and lower electrochemical materials. The outer edge of the membrane may or may not extend beyond the edge of the electrochemical materials, where examples of these differing aspects are reviewed in greater detail below.

FIG. 1 A provides a view of an aspect of an IEM according to the invention which has a membrane that extends beyond the outer edges of the electrochemical materials to provide a virtual dipole having a length that is longer than the actual dipole between the electrochemical materials. As shown in FIG. 1A, IEM 10 includes integrated circuit 2, having an upper electrochemical material 4 (which may comprise two distinct material layers) and a lower electrochemical material 6. Also shown is disc shaped membrane 8. FIG. 1 B provides an overhead view of the IEM shown in FIG. 1 A, depicting the disc shape of upper electrochemical material 4 and the positioning of the upper electrochemical material in the center of disc shaped membrane 8. The distance that the edge of the membrane may extend beyond the edge of electrochemical materials may vary, and in certain aspects is 0.05 mm or more, e.g., 0.1 mm or more, including 1.0 mm or more, such as 5.0 mm or more and including 1 0 mm or more, where the distance may not exceed 1 00 mm in certain aspects.

Figure 1B:
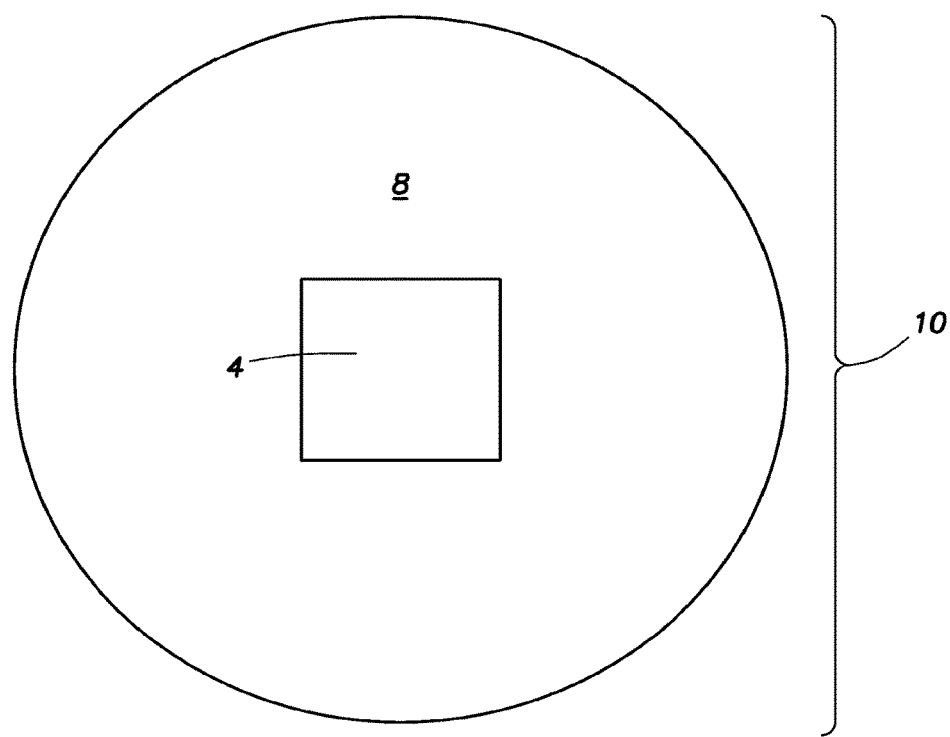
Figure 1C:
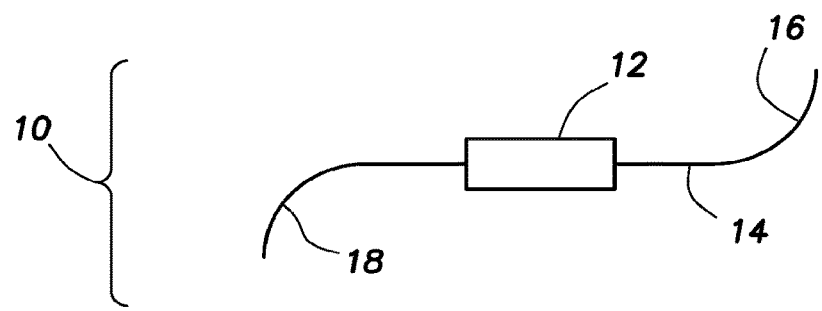
Figure 1D:
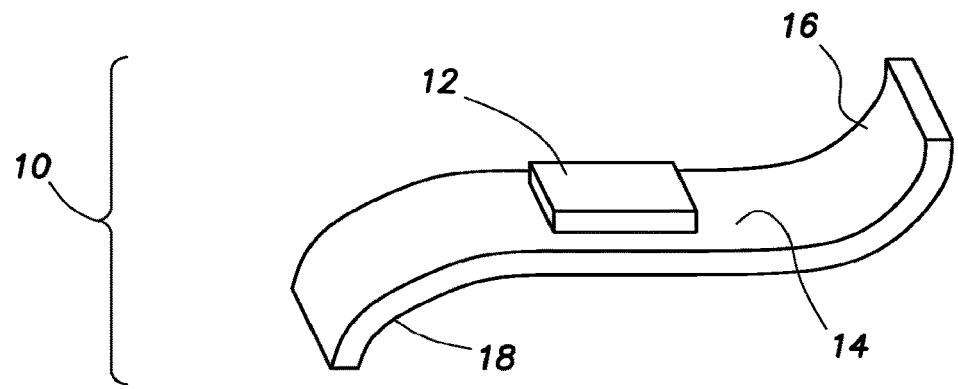

As can be seen in the aspect depicted in FIGS. 1A to 1B, the upper and lower electrochemical materials are planar electrochemical materials, where these electrochemical materials may have any convenient shape, e.g., square, disc, etc. The disc shaped membrane or amplifier 18 is a planar disc structure, where the edge of the membrane extends beyond the edge of the planar upper and lower electrochemical materials. In the depicted aspect, the radius of the membrane is longer than the radius of the upper and lower electrochemical materials, e.g., by 1 mm or more, such as by 10 mm or more.

Figure 1E:
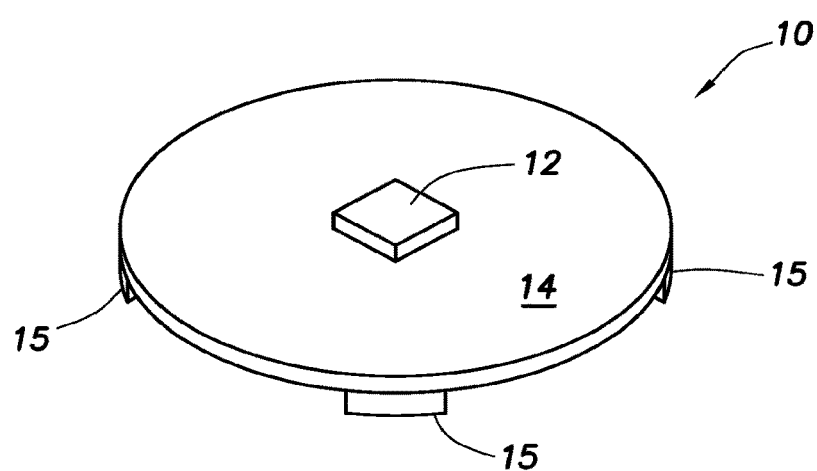
Figure 1F:
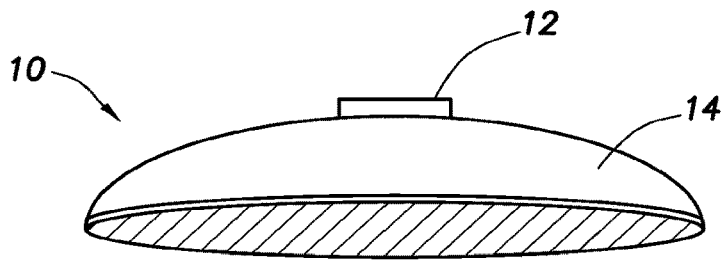

Membranes may have "two-dimensional" or "three-dimensional" configurations. Membrane configurations of interest are further described in PCT application serial no. US2008/077753 published as WO2009/042812, as well as U.S. provisional application Ser. Nos. 61/142,849 and 61/173,511; the disclosures of which are herein incorporated by reference. In some instances, IEMs of the invention include a membrane having a configuration that is chosen to provide for reduced susceptibility to signal-compromising events following contact with the target physiological site. One type of signal-compromising event that may occur is where the IEM adheres to a wall of the gastro-intestinal (GI) tract, such as the stomach wall, and thereby is prevented from interacting freely with fluid at the target physiological site. The membrane may be configured in a three-dimensional shape which discourages adhesion to a GI tract wall. One such configuration is shown in FIGS. 10 and 10. FIG. 10 provides a cross-sectional view of an IEM 10 that includes an IEM circuitry component 12 and a membrane 14 that has opposing curved edges 16 and 18. FIGS. 1E and 1F provide views of additional types of membranes having a three-dimensional shape that discourages adherence to a GI tract wall. In FIG. 1E, IEM 10 includes IEM circuitry component 12 centrally positioned in membrane 14. Membrane 14 includes projections 15 which prevent the bottom side of the IEM circuitry component 12 from lying flat on a GI tract wall. In FIG. 1F, IEM 10 includes IEM circuitry component 12 centrally positioned on membrane 14, where membrane 14 has a concave configuration which prevents the bottom side of the IEM circuitry component from lying flat on a GI tract wall.

Figure 2A:
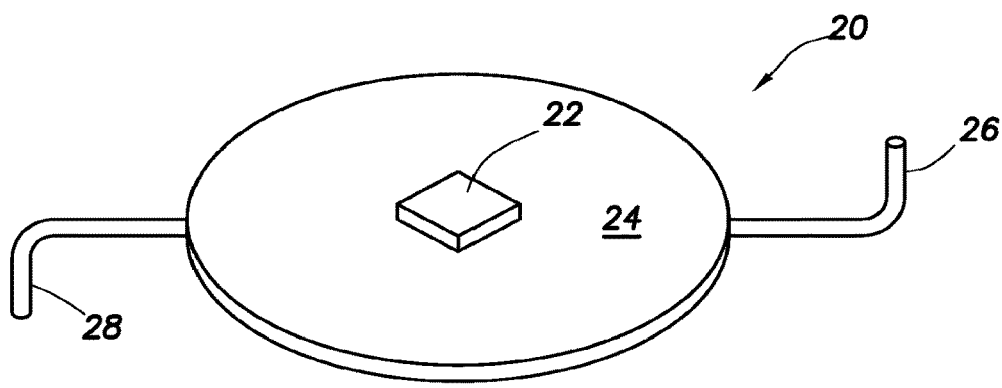
FIGS. 2A and 2B provide illustrations of an IEM that includes a membrane having deployable arms.
Figure 2B:
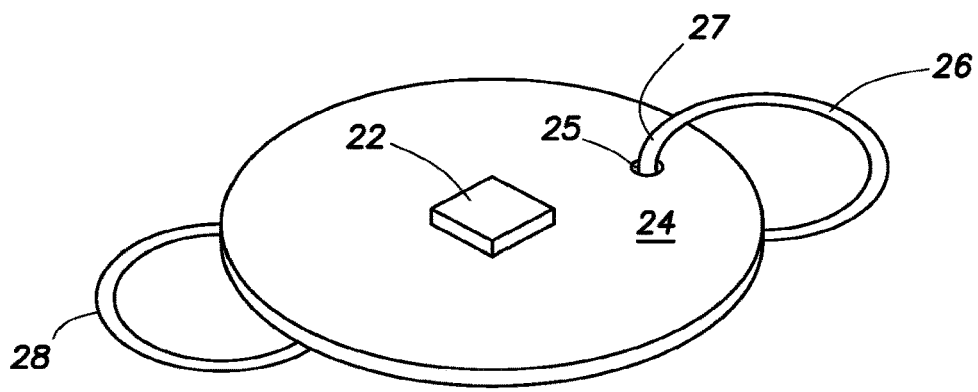

Alternatively, the membrane may include one or more deployable elements which serve to prevent the IEM from adhering to a GI tract wall. An example of such an IEM is shown in FIG. 2A, which depicts IEM 20 having IEM circuitry component 22 and membrane 24. Also shown in FIG. 2A are deployable elements 26 and 28 having opposing configurations. As these elements are deployable, they are present in a first configuration prior to IEM ingestion and then deploy to a second position following ingestion. A deployable configuration is depicted in FIG. 28, where IEM 20 of FIG. 2A is shown with the end 27 of arm 26 associated with the surface of the membrane 24, for example with a physiologically acceptable glue 25 that dissolves upon contact with an aqueous fluid. With respect to the IEM shown in FIG. 28, upon contact with a target physiological fluid, such as stomach fluid, the glue dissolves to deploy the arms, such that the IEM assumes the configuration shown in FIG. 2A.

Figure 3:
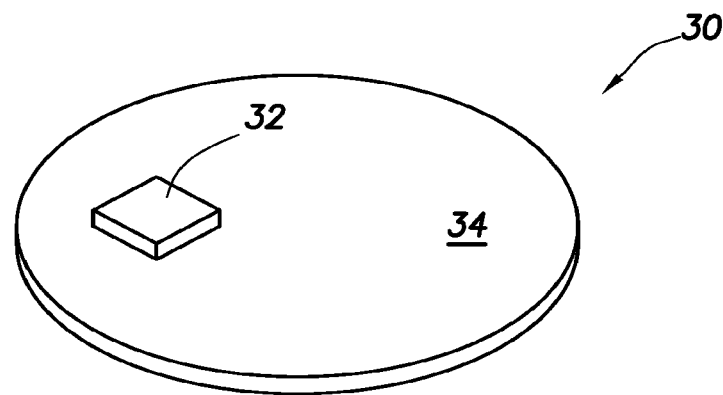
FIG. 3 provides a view of an IEM in which the IEM component is positioned off-center relative to the membrane.
Figure 4:
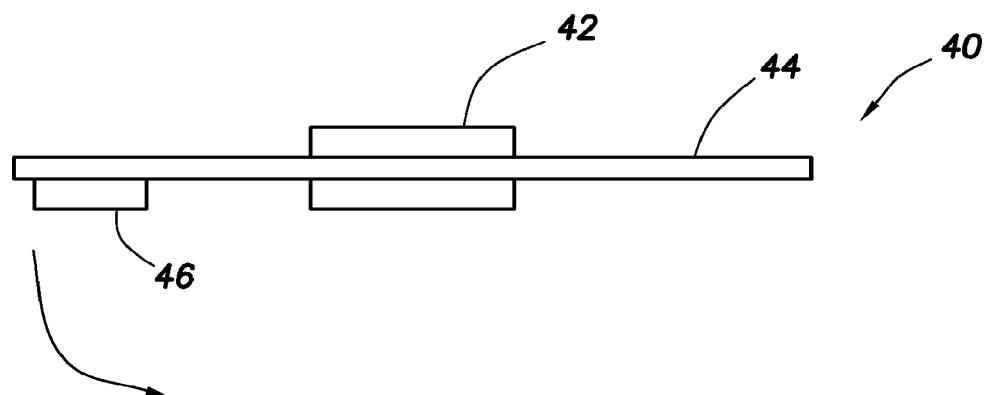
FIG. 4 provides a view of an IEM having a weight positioned on one side of the membrane.
Figure 5:
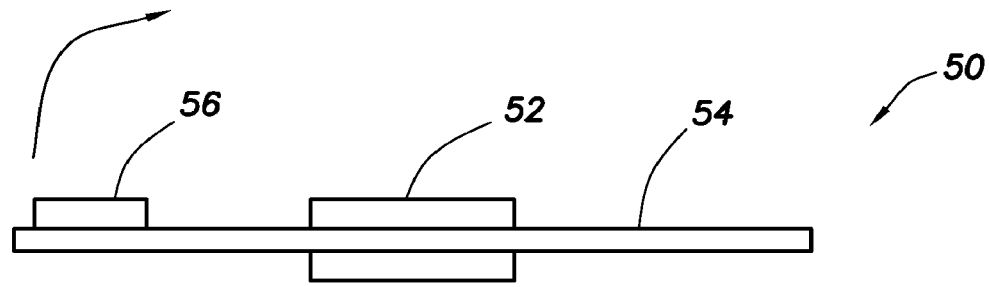
FIG. 5 provides a view of an IEM having a water-swellable component positioned on side of the membrane.

In yet another configuration of interest, the IEM circuitry component is non-centrically positioned relative to the membrane. An example of such an IEM is shown in FIG. 3, where IEM 30 includes IEM circuitry component 32 non-centrically positioned in the membrane 34.

Where desired, one or more components which promote movement of the IEM in a liquid environment, such as when present in stomach fluid, may be associated with the membrane. For example, an IEM may have a weight non-centrically associated with a membrane. An example of such a configuration is shown in FIG. 4. In FIG. 4, IEM 40 includes IEM circuitry component 42 and membrane 44. Also shown is weight 46 which is non-centrically associated with the membrane. Upon contact with a fluid, the weight serves to move the IEM in the direction of the arrow so that the IEM sinks into and becomes immersed in the fluid. In the aspect shown in FIG. 4, the weight has a density greater than that of stomach fluid and serves to pull the edge of the IEM with which the weight is associated down relative the opposite edge of the IEM. Instead of a weight, the IEM may have a swellable component non-centrically positioned on the membrane which, upon contact with an aqueous fluid, swells in a manner such that its density decreases relative to stomach fluid and it lifts one edge of the IEM relative to the opposing edge. An example of such an IEM is shown in FIG. 5, wherein IEM 50 includes IEM circuitry component 52 and -membrane 54, as well as water-swellable component 56. Water-swellable component 56 swells under aqueous conditions to lift one edge of the IEM relative to the opposite edge, as indicated by the arrow.

Figure 6A:
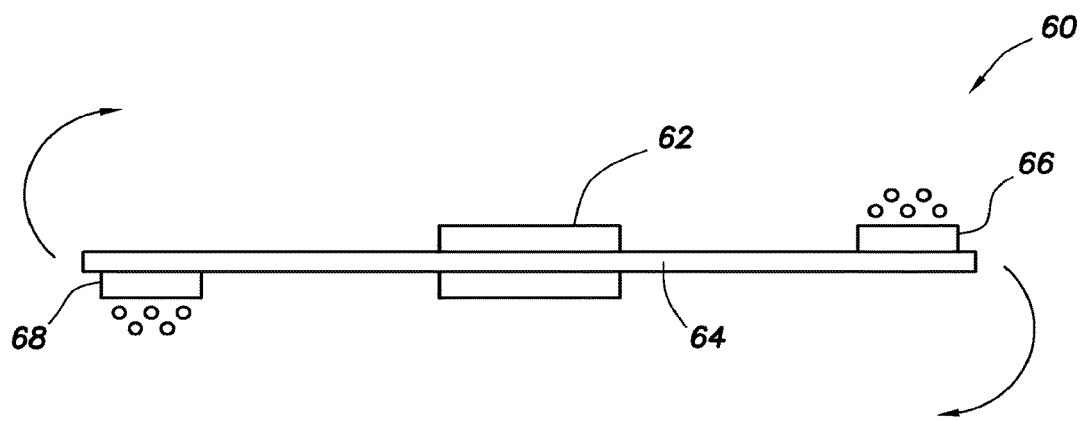
FIGS. 6A and 6B provide views of different IEM configurations which incorporate effervescent structures.
Figure 6B:
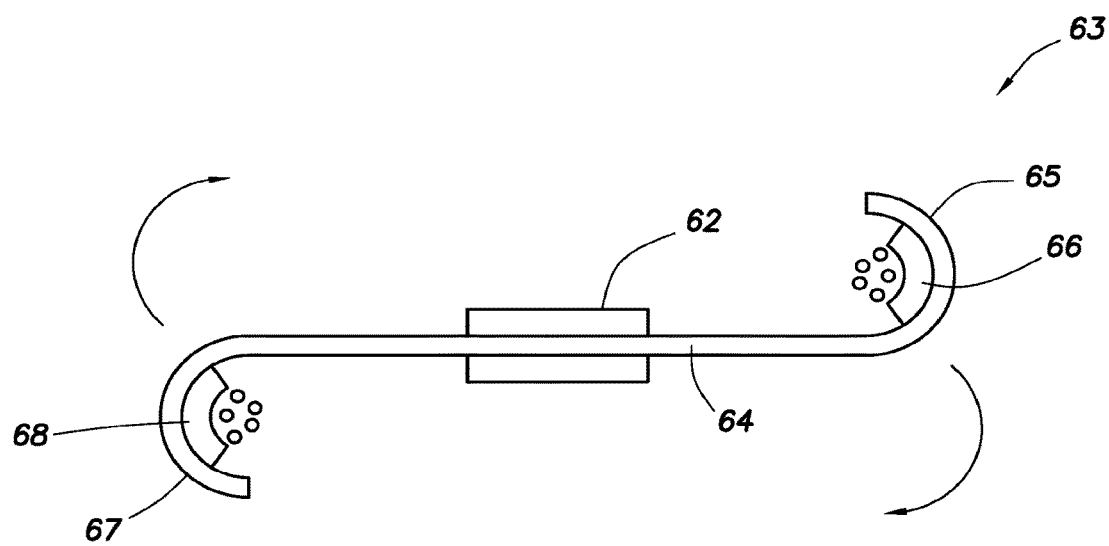

To enhance movement of the IEM when present in a liquid environment, such as a target physiological fluid, effervescent structures that generate bubbles upon contact with the target physiological fluid may be associated with one or more locations of the membrane. One or more distinct effervescent structures may be associated with the membrane. Of interest are membranes that include two distinct effervescent structures associated with opposing sides of the membrane, such that a first effervescent structure is present on a first side of the membrane and a second effervescent structure is present on a second side of the membrane. In this orientation, the effervescent structures, upon generation of bubbles, force the IEM to rotate in a liquid environment as a result of opposing forces applied to the edges of the membrane. Representations of IEMs that include effervescent structures are shown in FIGS. 6A and 6B. FIG. 6A shows an IEM 60 having IEM circuitry component 62 that is centrically positioned in membrane 64. Also shown are effervescent structures 66 and 68 which generate bubbles upon contact with a physiological fluid, as shown. The bubbles apply opposing forces to the edges of the membrane, causing the IEM to rotate as indicated by the arrows. In FIG. 6B, IEM 63 is analogous to IEM 60 of FIG. 6A, with the exception that the membrane has curved edges 65 and 67. The effervescent structure may include any convenient effervescent material that is physiologically acceptable and generates gas bubbles upon contact with an aqueous fluid, such as stomach fluid. The effervescent material may generate a variety of gasses, such as carbon dioxide, hydrogen, oxygen, and the like. Of interest in some instances are effervescent materials that include magnesium, which generates hydrogen gas upon contact with an aqueous physiological fluid. Other effervescent materials of interest include acid sources, such as but not limited to food acids, acid and hydrite antacids such as, for example, citric, tartaric, amalic, fumeric, adipic, and succinic acids. Carbonate sources of interest include, but are not limited to, dry solid carbonate and bicarbonate salt such as, sodium bicarbonate, sodium carbonate, potassium bicarbonate and potassium carbonate, magnesium carbonate and the like.

The membrane may be fabricated from a number of different materials, where the membrane may be made of a single material or be a composite of two or more different types of materials. In choosing a suitable material or materials, one characteristic of interest is mechanical strength. As indicated above, the membrane material may be a composite structure of two or more materials, e.g., an insulative material deposited on a metallic layer.

In certain instances, the membrane will have a mechanical strength sufficient to withstand the mechanical forces typical of the gastrointestinal (GI) tract without folding onto itself and losing its shape. This desired mechanical strength may be chosen to last for at least the duration of the communication, which may be 1 second or longer, such as at least 1 minute or longer, up to 6 hours or longer. In certain aspects, the desired mechanical strength is selected to least for a period of time ranging from 1 to 30 minutes. The desired mechanical strength can be achieved by proper selection of polymer or fillers, or mechanical design (e.g., lamination of multiple layers, or curvature of the amplifier surface) to increase the mechanical strength of the final structure.

Membranes of the invention are ones that are electrically insulating. As such, the materials from which the membranes are fabricated are electrically insulating materials. A given material is electrically insulating if it has a resistivity that is 2 times or greater than the medium in which the device operates (e.g., stomach fluid), such as 10 times or greater, including 100 times or greater than the medium in which the device operates.

Additional characteristics of interest for the membranes include ingestibility and low risk of blockage. It is desirable that the membrane be made of safe and ingestible material, such as food additives or pharmaceutical excipients. It may be further desirable to make the membrane in such a way to ensure low risk for blockage of the GI tract by one or more devices. This can be achieved via chemical or physical dissolution or digestion of the amplifier material, or mechanical breakdown of the membrane, or a combination of the two. For example, the membrane can contain one or more materials that chemically or physically dissolve in GI fluids after a certain amount of time. The material can also be selected to become soluble upon reaching certain parts of the GI tract where the chemical environment is different, for example, a change in pH (e.g., from pH 1-2 in stomach to pH >5 in intestine) or enzymatic components (such as enzymes present in the colon). The membrane may also be mechanically designed to have a weak point that dissolves and allows the entire structure to break up. The membrane may be constituted of several layers, for example an inner soluble or swelling layer and an outer layer that controls the dissolution rate of the inner layer; after a certain amount of time, the inner layer dissolves or swells, bursting apart the entire structure. The membrane does not need to be fully soluble or digestible to eliminate the risk of blockage; it is sufficient that the membrane becomes mechanically pliable or friable enough that it folds or breaks up under modest mechanical strain in the GI tract.

In certain aspects, the membrane may also serve as a reservoir of active pharmaceutical agents. The membrane will then serve the dual purpose of increase the dipole and serving as a drug depot. As summarized above, membranes of interest include an amount of a pharmaceutically active agent. The phrase "pharmaceutically active agent" (also referred to herein as drugs) refers to a compound or mixture of compounds which produces a physiological result, e.g., a beneficial or useful result, upon contact with a living organism, e.g., a mammal, such as a human. Pharmaceutically active agents are distinguishable from such components as excipients, carriers, diluents, lubricants, binders and other formulating aids, and encapsulating or otherwise protective components. The pharmaceutically active agent may be any molecule, as well as binding portion or fragment thereof, that is capable of modulating a biological process in a living subject. In certain aspects, the pharmaceutically active agent may be a substance used in the diagnosis, treatment, or prevention of a disease or as a component of a medication. In certain aspects, the pharmaceutically active agent may be a chemical substance, such as a narcotic or hallucinogen, which affects the central nervous system and causes changes in behavior.

The amount of pharmaceutically active agent that is present in the membrane may vary. In some instances, the amount of pharmaceutically active agent that is present in the membrane may range from 0.01 to 100% by weight. Specific pharmaceutically active agents of interest include, but are not limited to, those described and listed below.

Depending on the particular configuration of a membrane, the disposition of the pharmaceutically active agent in the membrane may vary. For example, the active agent may be homogeneously dispersed in the membrane. Alternatively, the active agent may be confined to a particular location or locations within the membrane, so that the membrane includes regions that have pharmaceutically active agent and regions that do not. An example of such a membrane is a membrane that is porous, where the pores of the membrane are filled with a pharmaceutically active agent. In such aspects, the porosity may range from 5 to 75% or more after swelling.

In some instances, the membrane is configured to provide for controlled release of the pharmaceutically active agent that is present in the membrane. By "controlled release" is meant that the membrane is configured such that the pharmaceutically active agent is released from the membrane upon contact with the target physiological site in a predetermined manner. In other words, pharmaceutically active agent is released from the membrane (upon contact with the target physiological site" in a way that has been predetermined, such as over an extended period of time, etc. As such, the pharmaceutically active agent is released from the membrane at predetermined intervals or gradually over a period of time.

The membrane can be configured to provide for controlled release of the pharmaceutically active agent using a variety of different approaches. For example, where the membrane is a homogenous structure, signal components or ingredients of the membrane may be chosen to provide for controlled release of the pharmaceutically active agent therefrom. Alternatively, where the membrane is porous, the porosity can be chosen to impart the desired controlled release characteristics to the membrane.

In yet other instances, one or more coating layers may be employed to impart controlled release characteristics to the membrane. In some instances, the release profile of the active agent from the membrane is controlled by a single coating applied to the membrane. In yet other aspects, a membrane may include two or more distinct coatings. In yet other instances, the coating layers may be fabricated from partly or entirely soluble polymer matrix materials which provide for a desired controlled release profile. Coatings of interest include those described in greater detail below.

In certain instances, the membrane has a multilayer configuration. Multilayered membrane configurations may be configured in a number of different ways. In some aspects, two or more of the different layers of the multilayered membrane may include the same active agent, where the multilayered configuration (for example where the two different layers have different compositions) provides for a desired controlled release profile of the active agent. In such aspects, the amount of active agent in each active agent comprising layer may be the same or different. In yet other aspects, two or more of the layers of a multilayered membrane may include different active agents.

Where desired, each layer of the multilayered membrane may include an IEM. In such instances, a given IEM will have a multilayered membrane where a distinct IEM is present in two or more layers of the multilayered membrane.

Where desired, the membrane may be configured such that the release of the active agent from the membrane is coupled to the activation of the event marker so that the IEM activation and communication coincides with active agent release, such as the precise start of the release of the active agent from the membrane.

As developed in further detail below, other components of the IEM may be configured to impart a controlled release profile to the active agent associated with the membrane, where these other components may be present instead of or in combination with membrane controlled release components, such as described above. For example, where the IEM includes a vehicle, such as a tablet or capsule, the vehicle may be configured to control release of the active agent from the membrane.

The membrane may be fabricated from various materials, categories of materials, and/or combinations of materials. Material categories of interest include, for example, but are not limited to: matrix materials; filler materials; soluble disintegrant materials; plasticizing agents; coatings; and wetting agents.

The surface of the membrane may also contain an anti-adhesion layer that prevents a transmitter from adhering to the stomach lining or getting blocked by objects in the GI tract such as food residue. An anti-adhesion film may also be used to prevent two or more devices from adhering to each other and blocking each other's communication.

In various aspects, the membrane may be fabricated from various materials, categories of materials, and/or combinations of materials. The categories include, for example, but are not limited to: film forming or binding/adhesive agents; fillers; soluble materials or disintegrants; plasticizing agents; coatings; and wetting agents.

The film forming or binding/adhesive agents include, for example, but are not limited to: agar; carageenan; cellulose acetate; chitosan; copovidone; ethyl cellulose; gelatin; gums (e.g., acacia, xanthan, guar, etc.); sugars (e.g., lactose, mannitol, xylitol, etc.); hydrogels (e.g., hydroxethyl cellulose, sodium alginate, urethane, etc.); acrylic acid polymers, cellulose acetate, hydroxypropylcellulose, hydroxypropylmethylcellulose, hydroxyethylcellulose, carboxymethylcellulose, ethylcellulose, methacrylic acid copolymer, methyl hydroxyethylcellulose, polyethylene glycol, polyvinyl acetate phthalate, polyvinyl alcohol, povidone, starch, carbomers, dextrin, hypromellose, poly(methylvinyl ether/maleic anhydride), chitosan, glyceryl monooleate, polyethylene oxide, polycarbophil, acacia, ceretonia, confectioner's sugar, cottonseed oil, dextrates, dextrose, glyceryl behenate, hydrogenated vegetable oil, hydroxypropyl starch, inulin, lactose, glucose, magnesium aluminum silicate, maltodextrin, maltose, methylcellulose, poloxamer, polycarbophil, polydextrose, polymethacrylates, stearic acid, sucrose, sunflower oil, zein, aluminum stearate, calcium silicate, colloidal silicon dioxide, glyceryl palmitostearate, pectin, polyethylene alkyl ethers, propylene carbonate, sodium ascorbate, zinc acetate, urethane, ammonium alginate, chlorpheniramine maleate, dibutyl phthalate, dibutyl sebacate, diethyl phthalate, dimethyl phthalate, ethyl lactate, vanillin, shellac, and the like.

The fillers include, for example, but are not limited to: oxides, e.g., titanium dioxide, magnesium oxide, etc.; silicates, e.g., magnesium silicate; phosphates, e.g., dicalcium phosphate; carbonates and bicarbonates; starches; cellulosic materials, e.g., microcrystalline cellulose; acacia, agar, alginic acid, carbomers, carboxymethylcellulose, carrageenan, cellulose acetate phthalate, ceratonia, chitosan, confectioner's sugar, copovidone, cottonseed oil, dextrates, dextrin, dextrose, ethylcellulose, gelatin, glyceryl behenate, guar gum, hydrogenated vegetable oil, hydroxyethyl cellulose, hydroxyethylmethyl cellulose, hydroxypropyl cellulose, hydroxypropyl starch, hypromellose, inulin, lactose, glucose, magnesium aluminum silicate, maltodextrin, maltose, methylcellulose, microcrystalline cellulose, poloxamer, polycarbophil, polydextrose, polyethylene oxide, polymethacrylates, povidone, sodium alginate, starch, stearic acid, sucrose, sunflower oil, zein, bentonite, calcium stearate, carbomers, cellulose, colloidal silicon dioxide, kaolin, maltitol, sesame oil, sodium starch glycolate, sorbitan esters, tragacanth, xanthan gum, mannitol, ammonium alginate, calcium carbonate, calcium phosphate, calcium sulfate, cellulose, cellulose acetate, erythritol, fructose, fumaric acid, glyceryl palmitostearate, isomalt, kaolin, lactitol, magnesium carbonate, magnesium oxide, mannitol, simethicone, trehalose, xylitol, and the like.

The soluble materials or disintegrants include, for example, but are not limited to: alginates (e.g., sodium or calcium); crosscarmellose sodium, carbpoxymethyl cellulose sodium, crospovidone, hydroxypropyl, cellulose, hydroxypropyl methyl cellulose, hypromellose, lactose mannitol, polyvinyl alcohol, and salts such as sodium or potassium chloride, alginic acid, calcium alginate, carboxymethylcellulose, cellulose, chitosan, colloidal silicon dioxide, croscarmellose sodium, crospovidone, docusate sodium, guar gum, hydroxypropyl cellulose, magnesium aluminum silicate, methylcellulose, microcrystalline cellulose, polacrilin potassium, povidone, sodium alginate, sodium starch glycolate, starch, and the like.

The plasticizing agents include, for example, but are not limited to dibutyl sebacate, triethyl citrate, andtriacetin, acetyltributyl citrate, acetyltriethyl citrate, benzyl benzoate, cellulose acetate phthalate, chlorbutanol, dextrin, dibutyl phthalate, dibutyl sebacate, diethyl phthalate, dimethyl phthalate, glycerin, glycerin monostearate, hypromellose phthalate, mannitol, mineral oil, lanolin alcohols, palmitic acid, polyethylene glycol, polymethacrylate, polyvinyl acetate phthalate, propylene glycol, 2-pyrolidone, sorbitol, stearic acid, triacetin, tributyl citrate, triethanolamine, triethyl citrate, and the like.

Coatings include, for example, but are not limited to polymethacrylates (pH sensitive) and polyvinyl acetate pthalate (pH sensitive), and hydroxypropyl methylcellulose (moisture barrier), acetyltributyl citrate, acetyltriethyl citrate, calcium carbonate, carboxymethylcellulose sodium, carnauba wax, cellulose acetate, cellulose acetate phthalate, cetyl alcohol, chitosan, ethylcellulose, fructose, gelatin, glycerin, glyceryl behenate, glyceryl palmitostearate, hydroxyethyl cellulose, hydroxyethylmethyl cellulose, hydroxypropyl cellulose, hypromellose, hypromellose phthalate, isomalt, glucose, maltitol, maltodextrin, methylcellulose, microcrystalline wax, paraffin, poloxamer, polydextrose, polyethylene glycol, polyvinyl acetate phthalate, polyvinyl alcohol, povidone, shellac, sucrose, titanium oxide, tributyl citrate, triethyl citrate, vanillin, xylitol, zein, talc, triethanolamine, ammonium alginate, chlorpheniramine maleate, copovidone, ethyl lactate, and the like. When present, coating layers may range in thickness from 0.1 to 200 μm thick, such as 1 to 100 or 1 to 100 μm. Of interest are coating layers that modulate release of the pharmaceutically active agent from the membrane upon contact with a target physiological site.

Wetting agents include, for example, polyethylene glycol, docusate sodium, sodium lauryl sulfate, polyethylene oxide, lecithin, poloxamer, and povidone, benzalkonium chloride, benzethonium chloride, cethylpyridinium chloride, docusate sodium, hypromellose, poloxamer, polythethylene alkyl ethers, polyoxyethylene alkyl ethers, polyoxyethylene castor oil derivatives, polyoxoethylene sorbitan fatty acid esters, polyoxyethylene stearates, sodium lauryl sulfate, sorbitan esters, benzyl alcohol, benzyl benzoate, cetylpyridinium chloride, cyclodextrins, glycerin monostearate, lecithin, meglumine, poloxomer, povidone, sodium bicarbonate, stearic acid, sulfobutylether beta-cyclodextrin, and the like.

The surface of the membrane may also contain an anti-adhesion layer that prevents an IEM from adhering to the stomach lining or getting blocked by objects in the GI tract such as food residue. An anti-adhesion film may also be used to prevent two or more devices from adhering to each other and blocking each other's communication. In these aspects, materials of interest for use in anti-adhesion layers include, but are not limited to: ethyl cellulose, microcrystalline cellulose, cellulose derivative, silicates, e.g., magnesium silicates or aluminum silicates, oxides, e.g., titanium oxide, etc. As indicated above, mixtures of the above materials or materials analogous thereto may be employed.

Of interest in certain aspects are anti-adhesion layers. In these aspects, materials of interest for use in anti-adhesion layers include, but are not limited to: ethyl cellulose, microcrystalline cellulose, cellulose derivative, silicates, e.g., magnesium silicates or aluminum silicates, oxides, e.g., titanium oxide, etc. As indicated above, mixtures of the above materials or materials analogous thereto may be employed.

Membranes may be fabricated using any convenient protocol. Membrane fabrication protocols of interest include, but are not limited to, those described in PCT/US08/77753, the disclosure of which is herein incorporated by reference.

Vehicle

Ingestible event markers may further include a vehicle component with which the IEM and membrane are stably associated. The vehicle component may be any convenient physiologically acceptable carrier composition. By "physiologically acceptable carrier composition" is meant a composition which is ingestible, where the composition may be solid or fluid. Solid vehicle configurations of interest include tablet and capsule configurations. The vehicle component, when present, may be fabricated from a variety of different materials. Materials of interest can be found in Remington's Pharmaceutical Sciences, Mace Publishing Company, Philadelphia, Pa., 17th ed. (1985).

As summarized above, ingestible event markers of the invention may combine one or more IEM/membrane components with a vehicle, where the vehicle may be any convenient physiologically acceptable carrier component. In some instances, the vehicle component is configured to impart a controlled release profile to the pharmaceutically active agent that is associated with the membrane. For example, the IEM/membrane component may be present inside of a solid tablet vehicle, where the solid tablet breaks down after a certain period of time following contact of the IEM with the target physiological site, to allow any active agent present in the IEM to be released.

A vehicle may be present even in those aspects where an active agent is not administered. In some aspects, vehicles are present to enhance ingestibility of an IEM. By stably associating the IEM to a vehicle such as a tablet or capsule (which may be conventionally sized or smaller), adherence of the IEM to the mouth can be avoided. In some instances the vehicle is a small tablet (i.e., mini-tablet) that is adhered to the ingestible event marker, for example with a physiologically acceptable adhesive.

Figure 7A:
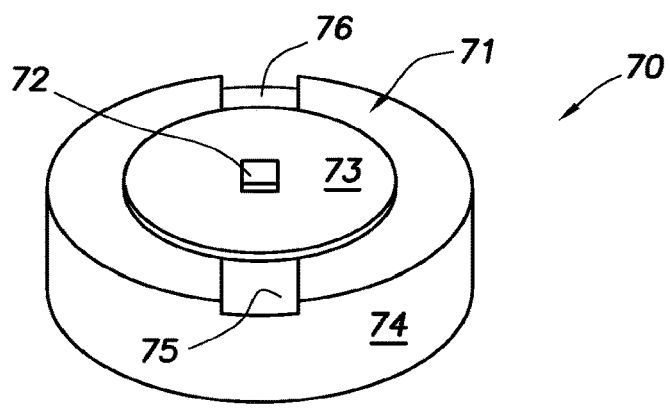
FIGS. 7A, 7B and 8 provide different views IEMs having a tablet configuration.
Figure 7B:
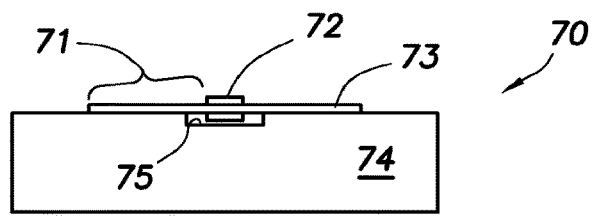
Figure 8:
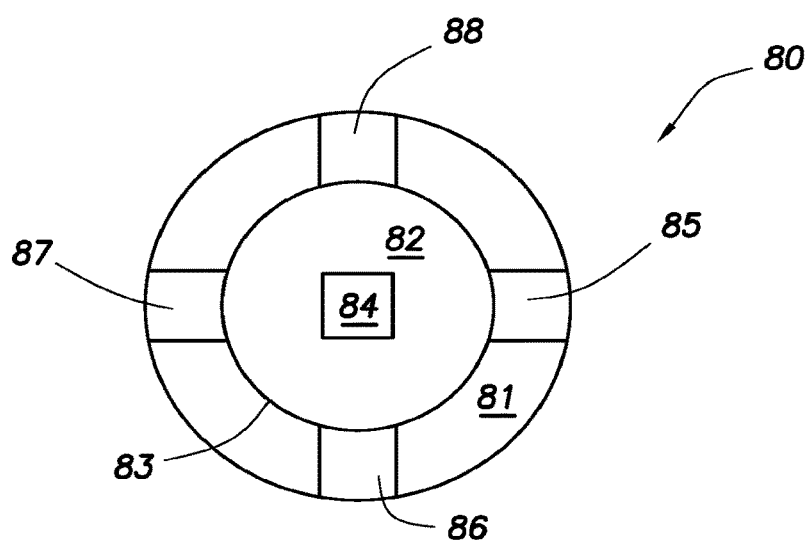

In some instances, IEMs are made up of an IEM stably associated with a solid vehicle component having a tablet configuration. In such instances, of interest are tablet vehicle components that are configured to promote contact of the electrochemical materials or IEM electrochemical materials with fluid upon contact of the IEM with the target physiological site. In such tablet configurations, the tablet may include one or more fluid passageways, such as grooves, channels, tubes or analogous structures, which serve to convey fluid from the environment of the IEM to an electrochemical material associated with a tablet vehicle. Passageway configurations of interest may also be configured to convey any bubbles generated at the electrochemical material component away from the electrochemical material component and/or to discourage formation of bubbles at the electrochemical material component. In such instances, the IEM is configured such that the electrochemical material is positioned relative to the passageway such that fluid in the passageway contacts the electrochemical material. An example of such an IEM is shown in FIG. 7. In FIG. 7, IEM 70 includes IEM 71 (made up of IEM circuitry component 72 and membrane 73) stably associated with the upper surface of tablet vehicle component 74. Also shown are channels 75 and 76 which are configured to provide a fluid passageway to the underside electrochemical material component of IEM circuitry component 72. FIG. 7B provides a cross-sectional view of IEM 70. In a given tablet configuration, the tablet may include one or more fluid passageways, where multiple fluid passageways may intersect, as desired to provide for desired movement gas bubbles. FIG. 8 provides an overhead view of another IEM 80 where tablet vehicle component 81 includes fluid passages ways 85, 86, 87 and 88 which intersect beneath the IEM 83 made up of IEM circuitry component 84 and membrane 82.

In these IEM configurations that include one or more fluid passageways, a given fluid passageway may be empty so as to provide uninhibited access of fluid to the electrochemical material component upon contact of the IEM with a fluid. Alternatively, the fluid passageway may be filled with a material that conveys the fluid from the environment to the electrochemical material component, such as material that wicks fluid from one location to another, a hydrogel material that absorbs fluid, and the like. Where desired, salts or other agents which control conductivity may be present.

Pharmaceutically Active Agent

Where desired, the IEM may include a pharmaceutically active agent. As indicated above, the pharmaceutically active agent, when present, may be present in the vehicle and/or membrane. As summarized above, membranes of the invention include an amount of an active agent, such as a pharmaceutically active agent or a diagnostic agent.

"Pharmaceutically Active agent" includes any compound or mixture of compounds which produces a physiological result, e.g., a beneficial or useful result, upon contact with a living organism, e.g., a mammal, such as a human. Pharmaceutically active agents (which may also be referred to herein as "drugs") are distinguishable from such components as excipients, carriers, diluents, lubricants, binders and other formulating aids, and encapsulating or otherwise protective components. The pharmaceutically active agent may be any molecule, as well as binding portion or fragment thereof, that is capable of modulating a biological process in a living subject. In certain aspects, the pharmaceutically active agent may be a substance used in the diagnosis, treatment, or prevention of a disease or as a component of a medication. In certain aspects, the pharmaceutically active agent may be a chemical substance, such as a narcotic or hallucinogen, which affects the central nervous system and causes changes in behavior.

The pharmaceutically active agent is capable of interacting with a target in a living subject. The target may be a number of different types of naturally occurring structures, where targets of interest include both intracellular and extracellular targets. Such targets may be proteins, phospholipids, nucleic acids and the like, where proteins are of particular interest. Specific proteinaceous targets of interest include, without limitation, enzymes, e.g., kinases, phosphatases, reductases, cyclooxygenases, proteases and the like, targets comprising domains involved in protein-protein interactions, such as the SH2, SH3, PTB and PDZ domains, structural proteins, e.g., actin, tubulin, etc., membrane receptors, immunoglobulins, e.g., IgE, cell adhesion receptors, such as integrins, etc., ion channels, transmembrane pumps, transcription factors, signaling proteins, and the like.

The pharmaceutically active agent may include one or more functional groups necessary for structural interaction with the target, e.g., groups necessary for hydrophobic, hydrophilic, electrostatic or even covalent interactions, depending on the particular drug and its intended target. Where the target is a protein, the pharmaceutically active agent may include functional groups necessary for structural interaction with proteins, such as hydrogen bonding, hydrophobic-hydrophobic interactions, electrostatic interactions, etc., and may include at least an amine, amide, sulfhydryl, carbonyl, hydroxyl or carboxyl group, such as at least two of the functional chemical groups.

Pharmaceutically active agents of interest may include cyclical carbon or heterocyclic structures and/or aromatic or polyaromatic structures substituted with one or more of the above functional groups. Also of interest as pharmaceutically active agents are compounds having structures found among biomolecules, including peptides, saccharides, fatty acids, steroids, purines, pyrimidines, derivatives, structural analogs or combinations thereof. Such compounds may be screened to identify those of interest, where a variety of different screening protocols are known in the art.

The pharmaceutically active agent may be derived from a naturally occurring or synthetic compound that may be obtained from a wide variety of sources, including libraries of synthetic or natural compounds. For example, numerous means are available for random and directed synthesis of a wide variety of organic compounds and biomolecules, including the preparation of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

As such, the pharmaceutically active agent may be obtained from a library of naturally occurring or synthetic molecules, including a library of compounds produced through combinatorial means, i.e., a compound diversity combinatorial library. When obtained from such libraries, the drug moiety employed will have demonstrated some desirable activity in an appropriate screening assay for the activity. Combinatorial libraries, as well as methods for producing and screening such libraries, are known in the art and described in U.S. Pat. Nos. 5,741,713; 5,734,018; 5,731,423; 5,721,099; 5,708,153; 5,698,673; 5,688,997; 5,688,696; 5,684,711; 5,641,862; 5,639,603; 5,593,853; 5,574,656; 5,571,698; 5,565,324; 5,549,974; 5,545,568; 5,541,061; 5,525,735; 5,463,564; 5,440,016; 5,438,119; 5,223,409, the disclosures of which are herein incorporated by reference.

Broad categories of active agents of interest include, but are not limited to: cardiovascular agents; pain-relief agents, e.g., analgesics, anesthetics, anti-inflammatory agents, etc.; nerve-acting agents; chemotherapeutic (e.g., anti-neoplastic) agents; neurological agents, e.g., anti-convulsants, etc.

Pharmaceutically active agents of interest include, but are not limited to: those listed in PCT application serial no. PCT/US2006/016370, the disclosure of which listed pharmaceutically active agents is incorporated herein by reference.

Salt

Where desired, a given IEM may include a non-active agent salt component, which component is made up of one or more non-active agent salts. In some instances, the amount of this salt component present in the IEM is chosen to be sufficient to enhance the strength of the communication generated by the IEM of the IEM when the IEM contacts the target physiological site, such as the stomach. The magnitude of communication strength enhancement may vary, where in some instances the magnitude of communication strength enhancement is 10× or more, such as 20× or more, including 50× or more, as compared to a suitable control (such as the strength of a communication generated by an analogous IEM which differs from the test IEM of interest solely by lack of the salt component). The amount of this non-active agent salt component is sufficient to provide for the desired communication strength enhancement. Non-active agent salts may vary, where non-active agent salts of interest include, but are not limited to: salts of physiologically acceptable electrolytes, such as but not limited to: sodium ion, chloride ion, potassium ion and calcium ion, magnesium ion, etc. Specific physiologically compatible salts of interest include, but are not limited to: KCl, NaCl, MgCl$_2$, and the like. When present, this non-active agent salt may be part of one or more of: the membrane, the IEM and the vehicle.

Anti-Foaming Agent

Also of interest are anti-foaming agents, which agents decrease the surface tension of gas bubbles. Anti-foaming agents of interest include, but are not limited to: silicone oil-based agents, such as simethicone, sorbitan sesquoleate, etc. When present, the amount of anti-foaming agent present in the IEM may vary, ranging from 0.01 to 10 mg, such as 0.1 to 100 µg, and including 0.1 to 10 µg. When present, this anti-foaming agent may be part of one or more of: the membrane, the IEM and the vehicle.

Surfactants

In some instances, the IEM includes one or more surfactants. Surfactants of interest include, but are not limited to: ionic surfactants, such as anionic surfactants, cationic surfactants and zwitterionic surfactants, as well as nonionic surfactants and surface active biological modifiers. Surfactants of interest include, but are not limited to: castor oil derivatives, cholesterol, polyglycolyzed glycerides, acetylated monoglycerides, sorbitan fatty acid esters, poloxamers, polysorbates, polyoxyethylene sorbitan fatty acid esters, polyoxyethylene compounds, monoglycerides or ethoxylated derivatives thereof, diglycerides or polyoxyethylene derivatives thereof, sodium docusate, sodium laurylsulfate, cholic acid or derivatives thereof, ethoxylated alcohols, ethoxylated esters, ethoxylated amides, polyoxypropylene compounds, propoxylated alcohols, ethoxylated/propoxylated block polymers, propoxylated esters, alkanolamides, amine oxides, fatty acid esters of polyhydric alcohols, ethylene glycol esters, diethylene glycol esters, propylene glycol esters, glycerol esters, polyglycerol fatty acid esters, SPAN™ surfactants, such as sorbitan esters), TWEEN™ surfactants, such as sucrose esters, glucose (dextrose) esters, alkali metal sulfates, quaternary ammonium compounds, amidoamines, and aminimides, simethicone, lecithins, alcohols, phospholipids, and mixtures thereof. When present, the surfactant component may be 0.01 to 10%, such as 0.01 to 100 ppm, including 0.1 to 100 ppm of the IEM composition. When present, surfactants may be part of one or more of: the membrane, the IEM and the vehicle.

Disintegrants

In some instances, the IEM compositions include one or more disintegrants. By disintegrant is meant an agent that enhances break up of at least some portion of the IEM, such as the vehicle or membrane, upon contact with the target physiological site. As such, disintegrants may facilitate mechanical disruption of the IEM vehicle component, such as a tablet, when the IEM contacts a fluid, such as stomach fluid. Disintegrants of interest include, but are not limited to, those disintegrants listed above, such as microcrystalline cellulose, starch, sodium starch glycolate, crosslinked polyvinylpyrrolidone, crosslinked carboxymethylcellulose, alginic acid, etc. When present, the disintegrant component may range from about 0.01 to 15%, such as 0.01 to 100 ppm, including 0.1 to 10 ppm of the IEM composition. When present, disintegrants may be part of one or more of: the membrane, the IEM and the vehicle.

Antioxidants

The IEM compositions may also include one or more antioxidants which serve to enhance shelf-life stability of the IEM. Antioxidants of interest include, but are not limited to: tocopherol and derivatives, ascorbic acid and derivatives, butylated hydroxyanisole, butylated hydroxytoluene, fumaric acid, malic acid, propyl gallate, metabisulfates and derivatives. When present, antioxidants may range from 0.01 to 10%, such as 0.01 to 100 ppm and including 0.1 to 1 ppm. When present, anti-oxidants may be part of one or more of: the membrane, the IEM and the vehicle.

Preservatives

IEMs of the invention may further include preservatives such as, but not limited to, benzalkonium chloride and derivatives, benzoic acid, benzyl alcohol and derivatives, bronopol, parabens, centrimide, chlorhexidine, cresol and derivatives, imidurea, phenol, phenoxyethanol, phenylethyl alcohol, phenylmercuric salts, thimerosal, sorbic acid and derivatives. The preservative may be present from in amounts ranging from 0.01 to 10 mg, such as 0.1 to 100 µg and including 0.1 to 1 µg. When present, preservatives may be part of one or more of: the membrane, the IEM and the vehicle.

Micro-Environment Modification Agents

IEMs of the invention may include one or more micro-environment modification agents that modify or control the micro-environment of an IEM upon contact with a target physiological site. Micro-environment modification agents of interest include but are not limited to surfactants, distintegrants, anti-oxidants, and preservatives. A given IEM may include one or more of these components as a micro-environment modification agent. Examples and amounts of each of these types of agents that may be present are provided above. When present, micro-environment modification agents may be part of one or more of: the membrane, the IEM and the vehicle.

Balanced Soluble/Insoluble Components

In some instances, IEM compositions of the invention are those in which the water insoluble and water soluble components of the vehicle are present in a ratio that is selected to provide for desired characteristics, such as dissolution of the vehicle, operations of the IEM, and the like. In some instances, the fraction of water insoluble components in the vehicle may range from 0.01 to 1, such as 0.1 to 0.9 and including 0.5 to 0.8. In some instances, the ingestible event marker has a fraction of soluble components up to 90% by weight.

Absorbent Component

An ingestible event marker may include a component that absorbs fluid, e.g., water, in order to increase the weight of the IEM (for example to ensure that the IEM sinks when it contacts fluid at a physiological site). This absorbent component may be the membrane, vehicle, or some distinct component of the IEM, such as an overlayer or coating, as desired. When present, this absorbent component may be fabricated from a variety of suitable materials, such as the hydrogel materials listed above.

Controlled Activation Element

IEMs of the invention may include a controlled activation element. The controlled activation element of the IEM that provides for controlled activation may be responsive to a variety of different types of stimuli. Stimuli of interest for which the controlled activation element can be configured to be responsive to include but are not limited to: liquid (wetting), time, pH, ionic strength, conductivity, biological molecules (e.g. specific proteins or enzymes that are present in the stomach, small intestine, colon), blood, temperature, specific auxiliary agents (foods ingredients such as fat, salt, or sugar, or other pharmaceuticals whose co-presence is clinically relevant), bacteria in the stomach, pressure, and light.

The controlled activation element is made up of one or more components that provides for the desired controlled activation functionality, such that the controlled activation element is responsive to the stimulus of interest. The nature of the component or components that make up the controlled activation element may vary. For example, where the stimulus of interest is temperature, the controlled activation element may be a barrier of a material, such as a film (e.g., a polymeric film) whose solubility is a function of temperature, specifically one that becomes soluble at or near body temperature. Such a film may be insoluble/impermeable to water at room temperature but soluble/permeable at 37° C. Materials of interest that may be used for such films include, but are not limited to the polymeric materials listed below. In those aspects where pressure is the stimuli of interest, the controlled activation element may be a pressure sensitive material, e.g., a capsule or shell (for example, made of a cellulosic material), that has a specific mechanical strength such that at a pressure threshold above the threshold the element will be crushed and allow the highly reliable event marker to be activated and communicate. In other aspects of interest, the stimulus may be light. For example, the stimulus may be a fluorescent label which has been attached to a tumor. As the IEM passes by the tumor, the controlled activation element may include a component that provides light at a stimulating wavelength for the label and also a component that detects emitted light from the label. Any convenient light source and detector may be employed. When the detector component detects the emitted light, it will activate the IEM in a controlled activation manner.

In certain aspects, the one or more controlled activation components of the invention provide for controlled activation, i.e., activation in a manner that is substantially, if not completely, independent of target site environment, as reviewed above. In one aspect of interest, the controlled activation component includes a dried conductive medium that, upon combination with target site fluid, produces an ionic medium in the presence of the first and second dissimilar materials to activate the battery, e.g., as reviewed above. When present, the dried conductive medium precursor may be any of a variety of different types of compositions. Compositions of interest include, but are not limited to: salts of physiologically acceptable electrolytes, such as but not limited to: sodium ion, chloride ion, potassium ion and calcium ion, magnesium ion, etc. Specific physiologically compatible salts of interest include, but are not limited to: KCl, NaCl, $MgCl_2$, and the like. Aspects of the invention include the presence of a dried conductive medium precursor. When the precursor is a salt, e.g., as described above, the dried salt may be provided in any convenient format, such as a lyophilized salt composition.

Controlled activation elements of interest are further described in PCT application serial no. PCT/US2007/082563 published as WO 2008/052136; the disclosure of which is herein incorporated by reference.

IEM Manufacture

A variety of manufacturing protocols may be employed to produce IEMs of the invention. Where the IEM does not include a vehicle, the IEM and membrane components may be produced as described above. Where the IEM further includes a vehicle, the IEM may be stably associated with the vehicle in some manner. By stably associated is meant that the IEM and the vehicle do not separate from each other, at least until administered to the subject in need thereof, e.g., by ingestion. The IEM may be stably associated with the vehicle in a number of different ways.

IEM fabrication protocols of interest include, but are not limited to, those described in PCT application serial nos. PCT/US2006/016370 and PCT/US08/77753; as well as in U.S. Provisional Application Ser. No. 61/142,849; the disclosures of which are herein incorporated by reference.

Systems

Also provided are systems that include an IEM and a communication detection component, e.g., in the form of a receiver, sometimes referred to herein as a "detector". Receivers of interest are those that are configured to receive a signal from an IEM. The detection component may vary significantly depending on the nature of the communication that is generated by the IEM. As such, the receiver may be configured to receive a variety of different types of communications, including but not limited to: RF signals, magnetic signals, conductive (near field) signals, acoustic signals, etc. In certain aspects, the receiver is configured to receive a signal conductively from an IEM, such that the two components use the body of the patient as a communication medium. As such, the signal that is transferred between the IEM and the receiver travels through the body, and requires the body as the conduction medium. The IEM emitted signal may be transmitted through and received from the skin and other body tissues of the subject body in the form of electrical alternating current (a.c.) voltage signals that are conducted through the body tissues. As a result, such aspects do not require any additional cable or hard wire connection, or even a radio link connection for transmitting the sensor data from the autonomous sensor units to the central transmitting and receiving unit and other components of the system, since the sensor data are directly exchanged via the skin and other body tissues of the subject. This communication protocol has the advantage that the receivers may be adaptably arranged at any desired location on the body of the subject, whereby the receivers are automatically connected to the required electrical conductor for achieving the communication, i.e., the communication is carried out through the electrical conductor provided by the skin and other body tissues of the subject.

The receiver may include a variety of different types of receiver elements, where the nature of the receiver element necessarily varies depending on the nature of the signal produced by the signal generation element. In certain aspects, the receiver may include one or more electrochemical materials (such as 2 or more electrochemical materials, 3 or more electrochemical materials, and/or includes multiple pairs of electrochemical materials, such as 2 or more, 3 or more, 4 or more pairs of electrochemical materials, etc., for detecting signal emitted by an IEM. In certain aspects, the receiver includes two or three electrochemical materials that are dispersed at a distance from each other, e.g., a distance that allows the electrochemical materials to detect a differential voltage. The distance between any two electrochemical materials may vary, and in certain aspects ranges from about 0.1 to about 5 cm, such as from about 0.5 to about 2.5 cm, e.g., about 1 cm.

In addition to receiving elements, such as electrodes electrochemical materials, receivers of the invention may include one or more integrated circuit components, one or more power components (such as power receivers or batteries), signal transmission components, housing components, etc.

The receivers of interest include both external and implantable receivers. In external aspects, the receiver is ex vivo, by which is meant that the receiver is present outside of the body during use. Where the receiver is implanted, the receiver is in vivo. The receiver is configured to be stably associated with the body, e.g., either in vivo or ex vivo, at least during the time that it receives the emitted signal from the IEM.

In certain aspects, the receiver is configured to provide data of a received signal to a location external to said subject. For example, the receiver may be configured to provide data to an external data receiver, e.g., which may be in the form of a monitor (such as a bedside monitor), a computer, a personal digital assistant (PDA), phone, messaging device, smart phone, etc. The receiver may be configured to retransmit data of a received signal to the location external to said subject. Alternatively, the receiver may be configured to be interrogated by an external interrogation device to provide data of a received signal to an external location.

Receivers of interest include, but are not limited to, those receivers disclosed in: PCT application serial nos. PCT/US2006/016370 published as WO 2006/116718; PCT/US2008/52845 published as WO 2008/095183; PCT/US2007/024225 published as WO 2008/063626 and PCT/US2008/085048; as well as U.S. Provisional Application Ser. No. 61/160,289; the disclosures of which applications (and particularly receiver components thereof) are herein incorporated by reference.

Systems of the invention may include an external device which is distinct from the receiver (which may be implanted or topically applied in certain aspects), where this external device provides a number of functionalities. Such an apparatus can include the capacity to provide feedback and appropriate clinical regulation to the patient. Such a device can take any of a number of forms. By example, the device can be configured to sit on the bed next to the patient, e.g., a bedside monitor. Other formats include, but are not limited to, PDAs, phones, such as smart phones, computers, etc. In some instances, the external device is configured to provide pharmacologic and physiologic information in a form that can be transmitted through a transmission medium, such as a telephone line, to a remote location such as a clinician or to a central monitoring agency. The external device can read out the information described in more detail in other sections of the subject patent application, both from pharmaceutical ingestion reporting and from physiological sensing devices, such as is produced internally by a pacemaker device or a dedicated implant for detection of the pill. The purpose of the external apparatus is to get the data out of the patient and into an external device. One feature of the external apparatus is its ability to provide pharmacologic and physiologic information in a form that can be transmitted through a transmission medium, such as a telephone line, to a remote location such as a clinician or to a central monitoring agency.

Methods

Aspects of the invention further include methods of using IEMs, such as those described above. Methods of the invention generally include administering an IEM to a subject, e.g., by self-administration or via the assistance of another, such as a health care practitioner. Generally, methods of the invention will include placing the IEM in the mouth of a subject such that the subject swallows the IEM. In this manner, the subject ingests the IEM. IEMs may be employed with a variety of subjects. Generally such subjects are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In certain aspects, the subjects will be humans.

Following ingestion, the methods include emitting one or more signals from the ingested IEM, for example when the IEM contacts the target physiological site. As reviewed above, the nature of the emitted signal may vary greatly. In some instances, the emitted signal is a conductively transmitted signal. Methods of the invention may also include receiving a signal emitted from an IEM, e.g., at a receiver, such as described above. In some instances, the received signal is a conductively transmitted signal.

IEMs may be employed in a variety of different applications, which applications may be both medical and non-medical in nature. Applications of interest include, but are not limited to: monitoring patient compliance with prescribed therapeutic regimens; tailoring therapeutic regimens based on patient compliance; monitoring patient compliance in clinical trials; monitoring usage of controlled substances; monitoring the occurrence of a personal event of interest, such as the onset of symptoms, etc., and the like. Applications of interest are further described in PCT application serial no. PCT/US2006/016370 published as WO/2006/116718; PCT application serial no. PCT/US2007/082563 published as WO/2008/052136; PCT application serial no. PCT/US2007/024225 published as WO/2008/063626; PCT application serial no. PCT/US2007/022257 published as WO/2008/066617; PCT application serial no. PCT/US2008/052845 published as WO/2008/095183; PCT application serial no. PCT/US2008/053999 published as WO/2008/101107; PCT application serial no. PCT/US2008/056296 published as WO/2008/112577; PCT application serial no. PCT/US2008/056299 published as WO/2008/112578; and PCT application serial no. PCT/US2008/077753; the disclosures of which are herein incorporated by reference.

Kits

Also provided are kits that include one or more IEMs, such as described above. In those aspects having a plurality of IEMs, the IEMs may be packaged in a single container, e.g., a single tube, bottle, vial, and the like, or one or more dosage amounts may be individually packaged such that certain kits may have more than one container of IEMs. In certain aspects the kits may also include a receiver, such as reviewed above. In certain aspects, the kits may also include an external monitor device, e.g., as described above, which may provide for communication with a remote location, e.g., a doctor's office, a central facility etc., which obtains and processes data obtained about the usage of the composition.

The subject kits may also include instructions for how to practice the subject methods using the components of the kit. The instructions may be recorded on a suitable recording medium or substrate. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other aspects, the instructions are present as an electronic storage data file present on a suitable computer readable storage medium, e.g. CD-ROM, diskette, etc. In yet other aspects, the actual instructions are not present in the kit, but means for obtaining the instructions from a remote source, e.g. via the internet, are provided. An example of this aspect is a kit that includes a web address where the instructions can be viewed and/or from which the instructions can be downloaded. As with the instructions, this means for obtaining the instructions is recorded on a suitable substrate.

Some or all components of the subject kits may be packaged in suitable packaging to maintain sterility. In many aspects of the subject kits, the components of the kit are packaged in a kit containment element to make a single, easily handled unit, where the kit containment element, e.g., box or analogous structure, may or may not be an airtight container, e.g., to further preserve the sterility of some or all of the components of the kit.

It is to be understood that this invention is not limited to particular aspects described, as such may vary. It is also to be understood that the terminology used herein is for the purpose of describing particular aspects only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual aspects described and illustrated herein has discrete components and features which may be readily separated from or combined with the features of any of the other several aspects without departing from the scope or spirit of the present invention. Any recited method can be carried out in the order of events recited or in any other order which is logically possible.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and aspects of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary aspects shown and described herein. Rather, the scope and spirit of present invention is embodied by the appended claims.

What is claimed is:

1. An ingestible event marker comprising:
   a support comprising a first external surface and a second external surface;
   a control circuit in contact with the support to control the event marker;
   a first electrochemical material in contact with the support and electrically coupled to the control circuit, wherein the first electrochemical material is positioned on the first external surface;
   a second electrochemical material electrically coupled to the control circuit and in contact with the support at a location different from the location of the first material, wherein the second electrochemical material is positioned on the second external surface, wherein positioning the first electrochemical material on the first external surface and the second electrochemical material on the second external surface is configured to electrically isolate the first and second electrochemical materials from each other, and wherein the first electrochemical material is dissimilar from the second electrochemical material; and a membrane physically associated with the support and positioned between the first electrochemical material and the second electrochemical material, wherein the membrane comprises an electrically insulative material, wherein the first electrochemical material, the second electrochemical material, and the membrane are configured to produce a dipole having a predefined dipole length based on the membrane, and wherein the membrane defines a concave shape configuration configured to prevent adherence of at least one of the first external surface and the second external surface to a target site; and wherein the control circuit is configured to generate a signal along a current path that employs a body as an electrically conductive medium upon the application of a voltage potential to the control circuit.

2. The ingestible event marker of claim 1, where the signal transmitted by the control circuit comprises pharmacologic information, physiologic information, or a combination thereof.

3. The ingestible event marker of claim 1, wherein the membrane comprises at least one projection.

4. The ingestible event marker of claim 1 wherein the membrane comprises at least one deployable element.

5. The ingestible event marker of claim 4, wherein the at least one deployable element comprises a plurality of arms, and wherein each of the plurality of arms defines a first configuration and a second configuration.

6. The ingestible event marker of claim 1, wherein the membrane comprises at least one of multiple coatings and multiple layers.

7. The ingestible event marker of claim 1, wherein the membrane is a composite structure made of at least two materials.

8. The ingestible event marker of claim 1, wherein the electrically insulative material is coupled to a metallic layer.

9. The ingestible event marker of claim 1, wherein the electrically insulative material is configured to dissolve in a predetermined amount of time when in contact with a physiological fluid.

10. The ingestible event marker of claim 1, further comprising a water-swellable component non-centrically associated with the membrane.

11. The ingestible event marker of claim 1, further comprising an active agent.

12. The ingestible event marker of claim 11, wherein the active agent is physically associated with the membrane and the membrane is configured to release the active agent in a phased manner.

13. The ingestible event marker of claim 11, wherein the active agent is comprised within at least one fluid passageway.

14. The ingestible event marker of claim 1, wherein the first and the second electrochemical materials are configured to generate a voltage potential to power the control circuit when the first and the second electrochemical materials come into contact with an electrically conductive liquid at a target physiological site.

15. An ingestible event marker comprising:
a support comprising a first external surface and a second external surface;
a control circuit in contact with the support to control the event marker;
a first electrochemical material in contact with the support and electrically coupled to the control circuit, wherein the first electrochemical material is positioned on the first external surface;
a second electrochemical material electrically coupled to the control circuit and in contact with the support at a location different from the location of the first material, wherein the second electrochemical material is positioned on the second external surface, wherein positioning the first electrochemical material on the first external surface and the second electrochemical material on the second external surface is configured to electrically isolate the first and second electrochemical materials from each other, and wherein the first electrochemical material is dissimilar from the second electrochemical material; and
a membrane physically associated with the support and positioned between the first electrochemical material and the second electrochemical material, wherein the membrane comprises an electrically insulative material, wherein the first electrochemical material, the second electrochemical material, and the membrane are configured to produce a dipole having a predefined dipole length based on the membrane, and wherein the membrane comprises a weight non-centrically associated with the membrane and configured to promote movement of the ingestible event marker in a liquid; and
wherein the control circuit is configured to generate a signal along a current path that employs a body as an electrically conductive medium upon the application of a voltage potential to the control circuit.

16. A system comprising:
an active agent; and
an ingestible event marker comprising:
a support comprising a first external surface and a second external surface;
a control circuit in contact with the support to control the event marker;
a first electrochemical material in contact with the support and electrically coupled to the control circuit, wherein the first electrochemical material is positioned on the first external surface;
a second electrochemical material electrically coupled to the control circuit, wherein the second electrochemical material is in contact with the support at a location different from the location of the first material to electrically isolate the first and second electrochemical materials from each other, wherein the second electrochemical material is positioned on the second external surface, and wherein the first electrochemical material is dissimilar from the second electrochemical material; and
a membrane physically associated with the support and positioned between the first electrochemical material and the second electrochemical material, wherein the membrane comprises an electrically insulative material, and wherein the first electrochemical material, the second electrochemical material, and the membrane are configured to produce a dipole having a predefined dipole length based on the membrane, and wherein the membrane defines a concave shape configuration configured to prevent adherence of at least one of the first external surface and the second external surface to a target site; and
wherein the control circuit is configured to generate a signal along a current path that employs a body as an electrically conductive medium upon the application of a voltage potential to the control circuit.

* * * * *

UNITED STATES PATENT AND TRADEMARK OFFICE
CERTIFICATE OF CORRECTION

Page 1 of 1

PATENT NO. : 10,588,544 B2
APPLICATION NO. : 15/050733
DATED : March 17, 2020
INVENTOR(S) : Hafezi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 322 days.

Signed and Sealed this
First Day of December, 2020

Andrei Iancu
*Director of the United States Patent and Trademark Office*